(12) United States Patent
Tanifuji et al.

(10) Patent No.: US 8,399,672 B2
(45) Date of Patent: *Mar. 19, 2013

(54) COMPOUND HAVING AFFINITY FOR AMYLOID

(75) Inventors: Shigeyuki Tanifuji, Chiba (JP); Daisaku Nakamura, Chiba (JP); Shinya Takasaki, Chiba (JP); Yuki Okumura, Chiba (JP)

(73) Assignee: Nihon Medi-Physics Co., Ltd., Tokyo (JP)

( * ) Notice: Subject to any disclaimer, the term of this patent is extended or adjusted under 35 U.S.C. 154(b) by 414 days.

This patent is subject to a terminal disclaimer.

(21) Appl. No.: 12/739,624

(22) PCT Filed: Oct. 24, 2008

(86) PCT No.: PCT/JP2008/069336
§ 371 (c)(1),
(2), (4) Date: Apr. 30, 2010

(87) PCT Pub. No.: WO2009/054497
PCT Pub. Date: Apr. 30, 2009

(65) Prior Publication Data
US 2010/0292479 A1    Nov. 18, 2010

(30) Foreign Application Priority Data

Oct. 26, 2007   (JP) ................................. 2007-278504

(51) Int. Cl.
*C07D 491/02* (2006.01)
*C07D 498/02* (2006.01)
(52) U.S. Cl. ...................................................... 546/121
(58) Field of Classification Search .................... 546/121
See application file for complete search history.

(56) References Cited

U.S. PATENT DOCUMENTS

| | | | | | |
|---|---|---|---|---|---|
| 4,727,145 | A | * | 2/1988 | Press ............................. | 546/121 |
| 4,791,117 | A | * | 12/1988 | Press ............................. | 514/300 |
| 6,103,724 | A | * | 8/2000 | Laszlovszky et al. ... | 514/252.16 |
| 6,436,939 | B2 | | 8/2002 | Carruthers et al. | |
| 6,489,337 | B1 | * | 12/2002 | Breitenbucher et al. ...... | 514/300 |
| 7,425,318 | B2 | | 9/2008 | Kung et al. | |
| 8,022,207 | B2 | * | 9/2011 | Tanifuji et al. ................. | 544/179 |
| 8,207,189 | B2 | * | 6/2012 | Tanifuji et al. ................. | 514/300 |
| 2006/0051293 | A1 | | 3/2006 | Kung et al. | |
| 2009/0252679 | A1 | | 10/2009 | Tanifuji et al. | |
| 2010/0069640 | A1 | * | 3/2010 | Tanifuji et al. ................. | 546/121 |
| 2010/0092387 | A1 | * | 4/2010 | Tanifuji et al. ................. | 424/1.85 |
| 2010/0249418 | A1 | * | 9/2010 | Tanifuji et al. ................. | 546/121 |
| 2010/0249419 | A1 | * | 9/2010 | Tanifuji et al. ................. | 546/121 |
| 2010/0267952 | A1 | * | 10/2010 | Tanifuji et al. ................. | 544/263 |

FOREIGN PATENT DOCUMENTS

| | | |
|---|---|---|
| JP | 2002-523383 T | 7/2002 |
| JP | 2004-506723 T | 3/2004 |
| JP | 2005-504055 T | 2/2005 |
| JP | 2005-512945 T | 5/2005 |
| WO | 00/10614 A1 | 3/2000 |
| WO | 01/74813 A2 | 10/2001 |
| WO | 01/74815 A2 | 10/2001 |
| WO | 02/16333 A2 | 2/2002 |
| WO | 02/085903 A2 | 10/2002 |
| WO | 03/018070 A1 | 3/2003 |
| WO | 03/106439 A1 | 12/2003 |
| WO | 2007/002540 A2 | 1/2007 |
| WO | 2007/063946 A1 | 6/2007 |
| WO | 2007/135890 A1 | 11/2007 |
| WO | 2007/148755 A1 | 12/2007 |
| WO | 2008/065785 A1 | 6/2008 |

OTHER PUBLICATIONS

Sanfilippo et al., Journal of Medicinal Chemistry (1988), 31(11), 2221-7.*
U.S. Appl. No. 12/226,561.
U.S. Appl. No. 12/227,487.
U.S. Appl. No. 12/308,715.
U.S. Appl. No. 12/312,596.
U.S. Appl. No. 12/312,867.
U.S. Appl. No. 12/739,348.
U.S. Appl. No. 12/740,580.
U.S. Appl. No. 12/740,627.
U.S. Appl. No. 12/740,646.
U.S. Appl. No. 12/740,658.

(Continued)

*Primary Examiner* — Niloofar Rahmani
(74) *Attorney, Agent, or Firm* — Fitch, Even, Tabin & Flannery, LLP

(57) ABSTRACT

A compound effective as a probe targeting amyloid for image diagnosis and a reagent comprising the compound for detecting amyloid deposited on a biological tissue are provided. Provided are a compound represented by the following formula (1):

wherein $R^1$, $R^2$ and $R^3$ independently represent a group selected from the group consisting of a hydrogen, hydroxyl group, alkyl substituent with 1 to 4 carbon atoms, alkoxy substituent having alkyl chain with 1 to 4 carbon atoms and halogen substituent, excluding the case where two or more of the substituents $R^1$, $R^2$ and $R^3$ are hydrogen, $R^4$ is a group selected from the group consisting of a hydrogen, hydroxyl group, alkoxy substituent having alkyl chain with 1 to 4 carbon atoms and halogen substituent, and m is an integer of 1 to 4, provided that at least one of $R^1$, $R^2$, $R^3$ and $R^4$ represents a radioactive halogen substituent, and a reagent comprising the same.

9 Claims, 5 Drawing Sheets

OTHER PUBLICATIONS

Supplementary European Search Report issued against European Patent Application 08841078.2 dated Jan. 23, 2012.
F. Dolle et al., "Radiosynthesis of 18F]PBR111, a selective radioligand for imaging the translocator protein (18 kDa) with PET", Journal of Labelled Compounds and Radiopharmaceuticals, vol. 51, No. 14, Nov. 1, 2008, pp. 435-439.
Chinese Office Action dated Mar. 1, 2012, issued against CN Patent Application 200880121679.2.
International Search Report issued on Nov. 25, 2008 in International Application No. PCT/JP2008/069336.
Office Action dated May 21, 2012 in Australian Application 2008314871.

* cited by examiner

COMPOUND HAVING AFFINITY FOR AMYLOID

CROSS REFERENCE TO RELATED APPLICATION

This application is a U.S. National Stage entry of International Application No. PCT/JP2008/069336 filed on Oct. 24, 2008, which claims priority to Japanese Application No. 2007-278504, filed on Oct. 26, 2007. The complete disclosures of the referenced international and priority application are incorporated herein by reference.

TECHNICAL FIELD

The present invention relates to a compound for use in diagnosis of cerebral degenerative disease. More specifically, the invention relates to a compound useful for amyloid detection at lesion sites in diagnosis of Alzheimer's disease and other diseases with amyloid accumulation.

BACKGROUND ART

Diseases with the onset of deposition of a fibrous protein called amyloid in various organs or tissues in bodies are generally referred to as amyloidosis. A feature common to amyloidosis is that the fibrous protein called amyloid which is enriched with the β-sheet structure is deposited at various organs systemically or at sites topically so that functional abnormalities are triggered in the organs or tissues.

Alzheimer's disease (hereinafter referred to as AD), which is a typical amyloidosis disease, is known as a disease causing dementia. This disease is lethal with progressive deposition of amyloid in brain, and thus is said to be a disease that causes concern in society compared with other amyloidosis diseases. In recent years, the number of AD patients is rapidly increasing in developed countries with aging societies, thereby causing a social problem.

From the pathohistological viewpoint, AD is characterized by three pathological findings in brain, namely development of senile plaques, formation of neurofibrillary tangles, and extensive neuronal loss. The senile plaque has a structure mainly composed of amyloid, and is said to appear at the earliest stage of AD onset and thus is pathologically found in brain about 10 or more years before appearance of clinical symptoms.

AD is diagnosed by carrying out various evaluations of cognitive functions (for example, Hasegawa scale, ADAS-JCog and MMSE) in auxiliary combination with imaging diagnosis such as CT and MRI. However, the method based on such evaluations of cognitive functions is low in diagnostic sensitivity at the early stage of the onset, and is furthermore problematic in that diagnostic results are susceptible to inborn cognitive functions of individuals. At present, it is practically impossible to establish a definite diagnosis of AD while an AD patient is still alive, because the definite diagnosis requires a biopsy of a lesion (Non-Patent Document 1).

Meanwhile, a report tells that amyloid constituting senile plaques is an aggregate of amyloid β protein (hereinafter referred to as Aβ). Also, numerous reports tell that the Aβ aggregate forms a β-sheet structure that causes nerve cell toxicity. Based on these findings, the so-called "Amyloid Cascade Hypothesis" is proposed, which suggests that cerebral deposition of Aβ triggers the downstream phenomena, namely, formation of neurofibrillary tangles and neuronal loss (Non-Patent Document 2).

Based on these facts, attempts have recently been made to detect AD in vivo using a compound having high affinity with amyloid as a marker.

Many of such probes for imaging diagnoses of cerebral amyloid are hydrophobic low-molecular weight compounds that are high in affinity with amyloid and high in cerebral transferability and are labeled with various radioactive species such as $^{11}C$, $^{18}F$ and $^{123}I$. For example, reports tell $^{11}C$ or radioactive halogen labeled forms of compounds including various thioflavin derivatives such as 6-iodo-2-[4'-(N,N-dimethylamino)phenyl]benzothiazole (hereinafter referred to as TZDM) and 6-hydroxy-2-[4'-(N-methylamino)phenyl]benzothiazole (hereinafter referred to as 6-OH-BTA-1) (Patent Document 1, Non-Patent Document 3); stilbene compounds such as (E)-4-methylamino-4'-hydroxystilbene (hereinafter referred to as SB-13) and (E)-4-dimethylamino-4'-iodostilbene (hereinafter referred to as m-I-SB) (Patent Document 2, Non-Patent Document 4, Non-Patent Document 5); benzoxazole derivatives such as 6-iodo-2-[4'-(N,N-dimethylamino)phenyl]benzoxazole (hereinafter referred to as IBOX) and 6-[2-(fluoro)ethoxy]-2-[2-(2-dimethylaminothiazol-5-yl)ethenyl]benzoxazole (Non-Patent Document 6, Non-Patent Document 7); DDNP derivatives such as 2-(1-{6-[(2-fluoroethyl)(methyl)amino]-2-naphthyl}ethylidene)malononitrile (hereinafter referred to as FDDNP) (Patent Document 4, Non-Patent Document 8); and imidazopyridine derivatives such as 6-iodo-2-[4'-(N,N-dimethylamino)phenyl]imidazo[1,2-a]pyridine (hereinafter referred to as IMPY) (Patent Document 3, Non-Patent Document 9). Further, some of these probes for imaging diagnosis have been studied on human imaging and have been reported to show a significant accumulation in AD patient's brain compared with normal persons (Non-Patent Document 10, Non-Patent Document 11, Non-Patent Document 12, Non-Patent Document 13).

International Publication No. WO2007/002540 pamphlet discloses a series of compounds with a group having affinity with amyloid, to which a radioisotope labeling site is attached via ethylene glycol or polyethylene glycol (Patent Document 5).

International Publication No. WO2007/063946 pamphlet discloses a series of compounds to which a five-membered aromatic heterocyclic group is attached in order to prevent them from being metabolized in brain (Patent Document 6).

[Patent Document 1] JP-T-2004-506723
[Patent Document 2] JP-T-2005-504055
[Patent Document 3] JP-T-2005-512945
[Patent Document 4] JP-T-2002-523383
[Patent Document 5] International Publication No. WO2007/002540 pamphlet
[Patent Document 6] International Publication No. WO2007/063946 pamphlet
[Non-Patent Document 1] J. A. Hardy & G. A. Higgins, "Alzheimer's Disease: The Amyloid Cascade Hypothesis.", Science, 1992, 256, p. 184-185
[Non-Patent Document 2] G. McKhann et al., "Clinical diagnosis of Alzheimer's disease: Report of the NINCDS-ADRDA Work Group under the auspices of Department of Health and Human Services Task Force on Alzheimer's Disease.", Neurology, 1984, 34, p. 939-944
[Non-Patent Document 3] Z.-P. Zhuang et al., "Radioiodinated Styrylbenzenes and Thioflavins as Probes for Amyloid Aggregates.", J. Med. Chem., 2001, 44, p. 1905-1914
[Non-Patent Document 4] Masahiro Ono et al., "11C-labeled stilbene derivatives as Aβ-aggregate-specific PET imaging agents for Alzheimer's disease.", Nuclear Medicine and Biology, 2003, 30, p. 565-571

[Non-Patent Document 5] H. F. Kung et al., "Novel Stilbenes as Probes for amyloid plaques.", J. American Chemical Society, 2001, 123, p. 12740-12741

[Non-Patent Document 6] Zhi-Ping Zhuang et al., "IBOX (2-(4'-dimethylaminophenyl)-6-iodobensoxazole): a ligand for imaging amyloid plaques in the brain.", Nuclear Medicine and Biology, 2001, 28, p. 887-894

[Non-Patent Document 7] Furumoto Y et al., "[11C]BF-227: A New 11C-Labeled 2-Ethenylbenzoxazole Derivative for Amyloid-β Plaques Imaging.", European Journal of Nuclear Medicine and Molecular Imaging, 2005, 32, Sup. 1, P759

[Non-Patent Document 8] Eric D. Agdeppa et al., "2-Dialkylamino-6-Acylmalononitrile Substituted Naphthalenes (DDNP Analogs): Novel Diagnostic and Therapeutic Tools in Alzheimer's Disease.", Molecular Imaging and Biology, 2003, 5, p. 404-417

[Non-Patent Document 9] Zhi-Ping Zhuang et al., "Structure-Activity Relationship of Imidazo[1,2-a]pyridines as Ligands for Detecting β-Amyloid Plaques in the Brain.", J. Med. Chem, 2003, 46, p. 237-243

[Non-Patent Document 10] W. E. Klunk et al., "Imaging brain amyloid in Alzheimer's disease with Pittsburgh Compound-B.", Ann. Neurol., 2004, 55, p. 306-319

[Non-Patent Document 11] Nicolaas P. L. G. Verhoeff et al., "In-Vivo Imaging of Alzheimer Disease β-Amyloid With [11C]SB-13 PET.", American Journal of Geriatric Psychiatry, 2004, 12, p. 584-595

[Non-Patent Document 12] Hiroyuki Arai et al., "[11C]-BF-227 AND PET to Visualize Amyloid in Alzheimer's Disease Patients", Alzheimer's & Dementia: The Journal of the Alzheimer's Association, 2006, 2, Sup. 1, S312

[Non-Patent Document 13] Christopher M. Clark et al., "Imaging Amyloid with I123 IMPY SPECT", Alzheimer's & Dementia: The Journal of the Alzheimer's Association, 2006, 2, Sup. 1, S342

DISCLOSURE OF THE INVENTION

Problems to be Solved by the Invention

As described above, various compounds are disclosed as probes for imaging diagnosis for amyloid, and researched for clinical application.

Experiments in normal mice show that [125I]-labeled TZDM, IBOX and m-I-SB are all transferred into brain 2 minutes after administration. However, these compounds are insufficient in clearance from normal tissues, and tend to accumulate gradually in brain as time passes after administration (JP-T-2005-512945; Zhi-Ping Zhuang et al., Nuclear Medicine and Biology, 2001, 28, p. 887-894; H. F. Kung et al., J. Am. Chem. Soc., 2001, 123, p. 12740-12741). When the clearance from normal tissues is insufficient, a problem arises in that sufficient contrast cannot be obtained at amyloid accumulation sites. [11C]-labeled SB-13 shows a clearance from normal tissues in experiments in rats, however, it cannot be said that the clearance is sufficiently fast (Masahiro Ono et al., Nuclear Medicine and Biology, 2003, 30, p. 565-571).

Meanwhile, it is revealed that compounds having an imidazopyridine skeleton such as IMPY have a property of transferring to brain and accumulating at amyloid after administration, and also have an excellent property of rapid clearance from normal tissues unlike the above-described compounds, as a result of experiments using [125I]-labeled compounds. However, IMPY is a compound positive in reverse mutation test. In order to use this compound as a probe for imaging diagnosis, sufficient care must be taken about dosage and administration manner (International Publication No. WO03/106439 pamphlet).

FDDNP is also reported to be positive in reverse mutation test. (International Publication No. WO03/106439 pamphlet)

The present invention has been made under such circumstances where various compounds have been disclosed as probes targeting amyloid for imaging diagnosis, but there has been no compound which is confirmed to have a clinically tolerable property, and aims at providing a compound that is effective as a probe targeting amyloid for imaging diagnosis and a reagent for detecting amyloid deposited on a biological tissue comprising the compound.

Means for Solving the Problems

As a result of intensive studies, the inventors have found that a compound effective as a probe targeting amyloid for imaging diagnosis can be provided by a series of compound with an imidazopyridine-phenyl skeleton in which various substituents are attached to the phenyl group thereof via an oxygen atom, and thus have completed the present invention.

According to one aspect of the present invention, a compound represented by the following formula (1):

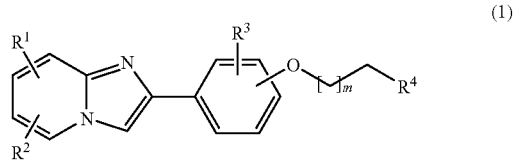

(1)

and a salt thereof, and a reagent for detecting amyloid deposited on a biological tissue comprising a compound represented by the formula (1) or a salt thereof are provided.

Here, a biological tissue can be various tissues at which amyloid is known to deposit in amyloidosis. Typical examples of such biological tissues include brain, heart, lung, pancreas, bone and joint, and as the most typical biological tissue, mention may be made of brain. The typical amyloidosis in case of brain includes Alzheimer's disease and dementia with Lewy bodies.

In the formula (1), $R^1$, $R^2$ and $R^3$ each independently represents a group selected from the group consisting of a hydrogen, a hydroxyl group, an alkyl substituent with 1 to 4 carbon atoms, an alkoxy substituent with an alky chain having 1 to 4 carbon atoms and a halogen substituent, provided that one in which two or more of the substituents $R^1$, $R^2$ and $R^3$ are hydrogenis excluded from the present invention.

$R^4$ is a group selected from the group consisting of a hydrogen, a hydroxyl group, an alkoxy substituent with an alky chain having 1 to 4 carbon atoms and a halogen substituent, and m is an integer of 1 to 4.

In addition, since the compound according to the present invention is used as a probe for image diagnosis, at least one of $R^1$, $R^2$, $R^3$ and $R^4$ is required to be a radioactive halogen.

As the radioactive halogen, a nuclide usually used in SPECT and PET can be used. More concretely, a radioactive halogen selected from the group consisting of $^{18}F$, $^{76}Br$, $^{123}I$, $^{124}I$, $^{125}I$ and $^{131}I$ can be used, and more preferably $^{18}F$ or $^{123}I$ can be used.

Therefore, according to the preferable embodiment, a compound of the present invention is selected from the group consisting of 2-[4'-(3"-fluoropropoxy)-3'-[$^{123}$I]iodophenyl]-6-methoxyimidazo[1,2-a]pyridine, 2-[4'-(2"-fluoroethoxy)-

3'-methoxyphenyl]-6-[$^{123}$I]iodoimidazo[1,2-a]pyridine, 2-[4'-(2"-fluoroethoxy)-3'-[$^{123}$I]iodophenyl]-6-methoxyimidazo[1,2-a]pyridine, 2-[4'-(2"-hydroxyethoxy)phenyl]-6-[$^{123}$I]iodo-7-methylimidazo[1,2-a]pyridine and 2-[4'-(2"-hydroxyethoxy)-2'-methoxyphenyl]-6-[$^{123}$I]iodoimidazo[1,2-a]pyridine, and a detecting reagent of the present invention comprises these compounds or a salt thereof.

According to another aspect of the present invention, a compound represented by any of the following formula (2):

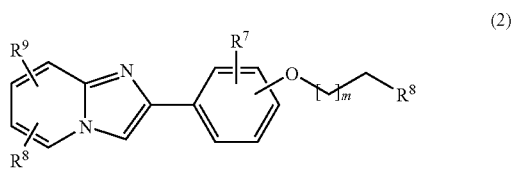

the following formula (3):

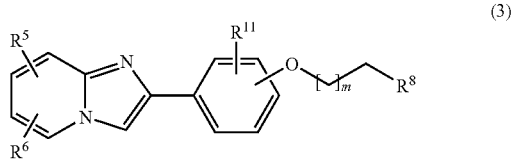

or the following formula (4):

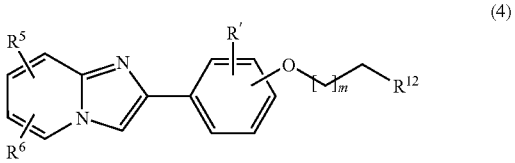

or a salt thereof is provided.

In the formulas (2), (3) and (4), $R^5$, $R^6$ and $R^7$ each independently represents a group selected from the group consisting of a hydrogen, a hydroxyl group, an alkyl substituent with 1 to 4 carbon atom, an alkoxy substituent with an alky chain having 1 to 4 carbon atoms and a halogen substituent, provided that one in which both $R^6$ and $R^7$ are hydrogen in the formula (2), one in which both $R^5$ and $R^6$ are hydrogen and in the formula (3), and one in which two or more of the substituents $R^5$, $R^6$ and $R^7$ are hydrogen in the formula (4) are excluded from the present invention.

$R^8$ is a group selected from the group consisting of a hydrogen, a hydroxyl group, an alkoxy substituent with an alkyl chain having 1 to 4 carbon atoms and a halogen substituent.

$R^9$ is a group selected from the group consisting of a non-radioactive halogen substituent, a nitro group, a trialkylammonium group having alkyl chains with 1 to 4 carbon atoms, a trialkylstannyl substituent having alkyl chains with 1 to 4 carbon atoms or a triphenylstannyl group.

$R^{11}$ is a group selected from the group consisting of a non-radioactive halogen substituent, a nitro group, a trialkylammonium group having alkyl chains with 1 to 4 carbon atoms, a trialkylstannyl substituent having alkyl chains with 1 to 4 carbon atoms or a triphenylstannyl group.

$R^{12}$ is a group selected from the group consisting of a non-radioactive halogen substituent, a methanesulfonyloxy substituent, a trifluoromethanesulfonyloxy substituent and an aromatic sulfonyloxy substituent.

Meanwhile, m is an integer of 1 to 4.

Effects of the Invention

The present invention provides a novel compound having affinity with amyloid and having an excellent capability of imaging amyloid in a living body, and a reagent for detecting amyloid deposited on a biological tissue.

BEST MODE FOR CARRYING OUT THE INVENTION (Synthesis of a Precursor Compound for a Radioactive Halogen-Labeled Compound)

Hereinafter, a method for synthesis of a compound according to the present invention will be described, taking the case of 6-tributylstannyl-2-[4'-(2"-fluoroethoxy)-3'-methoxyphenyl]imidazo[1,2-a]pyridine as an example.

For the synthesis of 6-tributylstannyl-2-[4'-(2"-fluoroethoxy)-3'-methoxyphenyl]imidazo[1,2-a]pyridine, first, 4'-hydroxy-3'-methoxyacetophenone is allowed to react with cupric bromide to prepare 2-bromo-4'-hydroxy-3'-methoxyacetophenone (FIG. 1, Step 1). This reaction can be conducted in accordance with ordinary methods, for example, the method described in a literature, King, L. Carroll & Ostrum, G. Kenneth, Journal of Organic Chemistry, 1964, 29(12), p. 3459-3461.

Then, 2-bromo-4'-hydroxy-3'-methoxyacetophenone as prepared above is allowed to react with 2-amino-5-iodopyridine to prepare 2-(4'-hydroxy-3'-methoxyphenyl)-6-iodoimidazo[1,2-a]pyridine (FIG. 1, Step 2). This step can be done, for example, according to the following procedure.

First, 2-bromo-4'-hydroxy-3'-methoxyacetophenone and 2-amino-5-iodopyridine are dissolved in an inactive solvent such as acetonitrile, and are allowed to react with each other at a reflux temperature for 2 to 6 hours to produce 2-(4'-hydroxy-3'-methoxyphenyl)-6-iodoimidazo[1,2-a]pyridine hydrobromide salt as white precipitates. The solvent used in this instance may be acetonitrile or another solvent that is usually employed in a similar reaction, for example, methanol and acetone. The reaction temperature may be a temperature allowing refluxing, for example, 110° C. when the solvent is acetonitrile. The amount of the solvent to be used may be an amount sufficient to effect the reaction, however, it should be noted that if the solvent is too much, it will become difficult to obtain precipitates of reaction products. For example, when 2-bromo-4'-hydroxy-3'-methoxyacetophenone in an amount corresponding to 2 mmol is used for the reaction, the amount of a solvent to be used can be about 15 to 30 mL.

Next, the reaction solution is filtered to recover the precipitates. The white precipitates are suspended in a mixed solution of methanol/water (1:3). Then, an aqueous saturated solution of sodium hydrogencarbonate is added thereto in a very excessive amount relative to the suspended precipitates to release 2-(4'-hydroxy-3'-methoxyphenyl)-6-iodoimidazo[1,2-a]pyridine as precipitates. The newly generated precipitates are filtered to recover 2-(4'-hydroxy-3'-methoxyphenyl)-6-iodoimidazo[1,2-a]pyridine as the target compound in this step (FIG. 1, Step 2). The amount of the mixed solution of methanol/water is not specifically limited as long as it is sufficient to effect the reaction. However, it should be noted that if the amount of the mixed solution is too much, precipitation of products will be hindered. For example, when 2-bromo-4'-hydroxy-3'-methoxyacetophenone in an amount corresponding to 2 mmol is used, the mixed solution of methanol/water may be used in an amount of about 4 to 10 mL. The amount of sodium hydrogencarbonate is not specifically limited as long as it is very excessive relative to the above-described precipitates as reaction substrates. For example, when the reaction is effected under the above-described conditions, the amount of an aqueous saturated solution of sodium hydrogencarbonate to be added to the reaction solution can be about 6 mL.

Then, the 2-(4'-hydroxy-3'-methoxyphenyl)-6-iodoimidazo[1,2-a]pyridine prepared above is sufficiently dried, dissolved in N,N-dimethylformamide, and potassium carbonate and 1-fluoro-2-paratoluensufonyloxyethane are added thereto. After this mixture was stirred at room temperature for about a day to effect the reaction, a saturated aqueous ammonium chloride solution is added followed by extraction with ethyl acetate, and the ethyl acetate layer is concentrated and subjected to chromatogram purification to obtain 2-[4'-(2''-fluoroethoxy)-3'-methoxyphenyl]-6-iodoimidazo[1,2-a]pyridine (FIG. 1, Step 3). The amount of potassium carbonate may be an amount that can neutralize paratoluenesulfonic acid which is generated during the reaction, and is typically about double to triple the other reactant 1-fluoro-2-paratoluenesulfonyloxyethane in molar ratio. Further, the 1-fluoro-2-paratoluenesulfonyloxyethane can be used in an excessive amount relative to the reaction substrate, and is typically about 1.5 times the reaction substrate 2-(4'-hydroxy-3'-methoxyphenyl)-6-iodoimidazo[1,2-a]pyridine in molar ratio.

The obtained 2-[4'-(2''-fluoroethoxy)-3'-methoxyphenyl]-6-iodoimidazo[1,2-a]pyridine is dissolved in dioxane, and triethylamine is added to the solution, followed by addition of bis(tributyltin) and a catalytic amount of tetrakis-triphenylphosphine palladium. This reaction solution is heated at about 90° C. to effect reaction for about a day, and then a solvent is distilled off and chromatographic purification is performed to obtain 6-tributylstannyl-2-[4'-(2''-fluoroethoxy)-3'-methoxyphenyl]imidazo[1,2-a]pyridine as the target compound (FIG. 2, Step 1). The amount of bis(tributyltin) to be used in this instance may be an amount satisfying a condition where it is excessive relative to the reaction substrate, specifically, it is about 1.5 times in molar ratio relative to the reaction substrate 2-[4'-(2''-fluoroethoxy)-3'-methoxyphenyl]-6-iodoimidazo[1,2-a]pyridine.

When a compound in which a trialkylstannyl substituent other than the tributylstannyl substituent is attached to the phenyl group is obtained, various bis(trialkyltin)s that fit purposes can be used instead of bis(tributyltin) in FIG. 2, Step 1. For example, when a compound having a trimethylstannyl substituent as a substituent at the 3'-position of the phenyl group is synthesized, a reaction similar to the above can be performed using bis(trimethyltin) in FIG. 2, Step 1.

When a compound with an imidazopyridine ring in which the binding site for the substituent is different or a compound to which two substituents are attached is obtained, various compounds that depend upon target compounds can be used instead of 2-amino-5-iodopyridine in Step 2 to effect the reaction in accordance with the conventional method.

For example, when a compound in which an iodo substituent is attached to 6-position and a methyl substituent is attached to 7-position of the imidazopyridine ring, 2-amino-4-methyl-5-iodopyridine may be used instead of 2-amino-5-iodopyridine in Step 2 to perform a reaction similar to the above in Step 2.

(A Method for Synthesis of a Radioactive Halogen-Labeled Compound)

Next, a method for production of a radioactive halogen-labeled compound according to another aspect of the present invention will be described, taking the case of radioactive iodine-labeled compounds as an example.

The synthesis of radioactive iodine-labeled compounds can be performed by dissolving the labeling precursor compound prepared as above procedure in an inert organic solvent, adding thereto a [$^{123}$I]sodium iodide solution or the like obtained by known methods, and adding thereto an acid and an oxidizing agent to effect the reaction. As an inert organic solvent dissolving the labeling precursor compound, various solvents having no reactivity with the labeling precursor, [$^{123}$I]sodium iodide and the like can be used, and preferably methanol can be used.

As the acid, may be used various ones, and preferably hydrochloric acid.

The oxidizing agent is not particularly limited as long as it can effect the oxidation of iodine in the reaction solution, and is preferably hydrogen peroxide or peracetic acid. The amount of the oxidizing agent to be added may be an amount sufficient to oxidize iodine in the reaction solution.

A compound labeled with a radioactive halogen other than iodine can be synthesized by labeling a labeling precursor that fits a purpose of synthesis with a radioactive halogen that fits the purpose.

(Methods for Preparing and Using a Diagnostic Agent in Accordance with the Present Invention)

The diagnostic agent according to the present invention can be prepared as a solution which comprises the present radioactive halogen-labeled compound blended in water, a physiological saline solution or a Ringer's solution optionally adjusted to an appropriate pH, like other commonly-known radioactive diagnostic agents. In this instance, concentration of the present compound should be adjusted to not more than the concentration at which stability of the present compound is ensured. Dosage of the present compound is not specifically limited as long as it is sufficient to obtain an image of distribution of an administered agent. For example, in case of iodine-123 ($^{123}$I)-labeled compounds and fluorine-18 ($^{18}$F)-labeled compounds, about 50 to 600 MBq per adult body of 60 kg weight can be administered intravenously or locally. Distribution of administered agents can be imaged by known methods. For example, iodine-123 ($^{123}$I)-labeled compounds can be imaged by a SPECT apparatus while fluorine-18 ($^{18}$F)-labeled compounds can be imaged by a PET apparatus.

Hereinafter, the present invention is described below in more detail by way of Examples, Comparative Examples and Reference Examples. However, these Examples never limit the scope of the present invention. Meanwhile, in the following Examples, the names of the individual compounds used in the experiment are defined as shown in Table 1.

TABLE 1

| Compound name | Common name |
| --- | --- |
| Compound 1 | 2-[4'-(3''-fluoropropoxy)-3'-[$^{123}$I]iodophenyl]-6-methoxyimidazo[1,2-a]pyridine |
| Compound 2 | 2-[4'-(2''-fluoroethoxy)-3'-methoxyphenyl]-6-[$^{123}$I]iodoimidazo[1,2-a]pyridine |
| Compound 3 | 2-[4'-(2''-fluoroethoxy)-3'-[$^{123}$I]iodophenyl]-6-methoxyimidazo[1,2-a]pyridine |
| Compound 4 | 2-[4'-(2''-hydroxyethoxy)phenyl]-6-[$^{123}$I]iodo-7-methylimidazo[1,2-a]pyridine |
| Compound 5 | 2-[4'-(3''-fluoropropoxy)-3'-iodophenyl]-6-methoxyimidazo[1,2-a]pyridine |
| Compound 6 | 2-[4'-(2''-hydroxyethoxy)-2'-methoxyphenyl]-6-[$^{123}$I]iodoimidazo[1,2-a]pyridine |

EXAMPLE 1

Synthesis of 2-[4'-(2"-fluoroethoxy)-3'-methoxyphenyl]-6-iodoimidazo[1,2-a]pyridine (non-radioactive iodinated form)

50 mL of ethyl acetate was added to 8.47 g (corresponding to 37.9 mmol) of cupric bromide to obtain a suspension, to which 3.00 g (corresponding to 18.1 mmol) of 4'-hydroxy-3'-methoxyacetophenone was added. Then, the resulting mixture was heated under reflux. After 2 hours, the reaction mixture was cooled down to room temperature and filtered. The resulting filtrate was concentrated under reduced pressure. The resulting crude product was purified by flash silica gel column chromatography (elution solvent: hexane/ethyl acetate=4/1), to obtain 4.11 g (corresponding to 16.3 mmol) of 2-bromo-4'-hydroxy-3'-methoxyacetophenone (FIG. 1, Step 1).

490 mg (corresponding to 2.00 mmol) of 2-bromo-4'-hydroxy-3'-methoxyacetophenone and 440 mg (corresponding to 2.00 mmol) of 2-amino-5-iodopyridine were dissolved in 15 mL of acetonitrile. The resulting solution was heated under reflux in an oil bath at 110° C. for 2 hours. After the completion of the reaction, the reaction solution was cooled down to room temperature, and precipitates were filtered and recovered. The precipitates were washed with acetonitrile and dried under reduced pressure. The resulting crude crystals were suspended in a mixed solution of 3.0 mL of water and 1.0 mL of methanol. Then, about 6.0 mL of a saturated sodium hydrogencarbonate solution was added thereto, and the mixture was sonicated for 5 minutes using an ultrasonic washing machine. Precipitates were filtered and recovered from the resulting mixture, sufficiently washed with water, and dried under reduced pressure, to obtain 231 mg (corresponding to 0.628 mmol) of 2-(4'-hydroxy-3'-methoxyphenyl)-6-iodoimidazo[1,2-a]pyridine (FIG. 1, Step 2).

231 mg (corresponding to 0.628 mmol) of 2-(4'-hydroxy-3'-methoxyphenyl)-6-iodoimidazo[1,2-a]pyridine that was sufficiently dried to remove moisture was dissolved in 6.0 mL of N,N-dimethylformamide, and 260 mg (corresponding to 1.88 mmol) of potassium carbonate was added thereto. Then, 206 mg (corresponding to 0.942 mmol) of 1-fluoro-2-parasulfonyloxyethane was added thereto, and the reaction mixture was stirred at room temperature for 18 hours. After the completion of the reaction, a saturated aqueous ammonium chloride solution was added thereto, and extracted three times with ethyl acetate. The combined ethyl acetate layers were washed with water and saturated sodium chloride solution, and then dried over anhydrous sodium sulfate, and concentrated under reduced pressure. The resulting crude product was purified by silica gel column chromatography (elution solvent: hexane/ethyl acetate=1/1) to obtain 235 mg (corresponding to 0.642 mmol) of 2-[4'-(2"-fluoroethoxy)-3'-methoxyphenyl]-6-iodoimidazo[1,2-a]pyridine (FIG. 1, Step 3).

The NMR measurement results of the resulting 2-[4'-(2"-fluoroethoxy)-3'-methoxyphenyl]-6-iodoimidazo[1,2-a]pyridine (internal standard: tetramethylsilane) are shown below.

NMR apparatus employed: JNM-ECP-500 (manufactured by Japan Electron Optics Laboratory Co., Ltd. (JEOL))

$^1$H-NMR (solvent: chloroform-d1; resonance frequency: 500 MHz): δ 8.37 (s, 1H), 7.75 (s, 1H), 7.57 (d, J=2.3 Hz, 1H), 7.42-7.40 (m, 2H), 7.34 (dd, J=1.8, 9.6 Hz, 1H), 6.97 (d, J=8.7 Hz, 1H), 4.80 (dt, $^2J_{HF}$=47.7 Hz, J=4.1 Hz, 2H), 4.31 (dt, $^3J_{HF}$=27.5 Hz, J=4.1 Hz, 2H), 3.99 (s, 3H).

EXAMPLE 2

Synthesis of 6-tributylstannyl-2-[4'-(2"-fluoroethoxy)-3'-methoxyphenyl]imidazo[1,2-a]pyridine 167 mg (corresponding to 0.427 mmol) of 2-[4'-(2"-fluoroethoxy)-3'-methoxyphenyl]-6-iodoimidazo[1,2-a]pyridine obtained in Example 1 was dissolved in 7.0 mL of dioxane, and 3.0 mL of triethylamine was added thereto. Then, 0.32 mL (corresponding to 0.64 mmol) of bis(tributyltin) and 32.6 mg (a catalytic amount) of tetrakis-triphenylphosphine palladium were added thereto. After the reaction mixture was stirred at 90° C. for 18 hours, the solvent was distilled off under reduced pressure. The residue was purified by flash silica gel column chromatography (elution solvent: hexane/ethyl acetate=2/1), to obtain 142 mg (corresponding to 0.247 mmol) of 6-tributylstannyl-2-[4'-(2"-fluoroethoxy)-3'-methoxyphenyl]imidazo[1,2-a]pyridine (FIG. 2, Step 1).

The NMR measurement results of the resulting 6-tributylstannyl-2-[4'-(2"-fluoroethoxy)-3'-methoxyphenyl]imidazo[1,2-a]pyridine (internal standard: tetramethylsilane) are shown below.

NMR apparatus employed: JNM-ECP-500 (manufactured by Japan Electron Optics Laboratory Co., Ltd. (JEOL))

$^1$H-NMR (solvent: chloroform-d1; resonance frequency: 500 MHz): δ 7.97 (s, 1H), 7.77 (s, 1H), 7.60-7.58 (m, 2H), 7.43 (dd, J=1.4, 8.2 Hz, 1H), 7.15 (d, J=8.7 Hz, 1H), 6.97 (d, J=8.2 Hz, 1H), 4.80 (dt, $^2J_{HF}$=47.2 Hz, J=4.1 Hz, 2H), 4.32 (dt, $^3J_{HF}$=27.0 Hz, J=4.1 Hz, 2H), 3.99 (s, 3H), 1.59-1.52 (m, 6H), 1.39-1.32 (m, 6H), 1.19-1.05 (m, 6H), 0.91 (t, J=7.3 Hz, 9H).

EXAMPLE 3

Synthesis of 2-[4'-(3"-fluoropropoxy)-3'-iodophenyl]-6-methoxyimidazo[1,2-a]pyridine (non-radioactive iodinated form)

100.0 g (corresponding to 0.575 mol) of 2-bromo-3-hydroxypyridine was dissolved in 310 mL of dimethylsulfoxide, and 575 mL (corresponding to 0.575 mol) of a 1 mol/L sodium methoxide-methanol solution was added thereto. Then, the reaction solution was heated to 90° C. to distill off methanol. After the reaction solution was cooled down to 10° C. or lower, 93.9 g (corresponding to 0.662 mol) of methyl iodide was added, and then stirred at room temperature for 20.5 hours. After the completion of the reaction, the reaction solution was poured into ice water and extracted twice with chloroform. The combined chloroform layer was washed with a 1 mol/L sodium hydroxide solution, washed twice with a saturated sodium chloride solution, and dried over anhydrous sodium sulfate. After the solvent was distilled off under reduced pressure, 65.4 g (corresponding to 0.348 mol) of 2-bromo-3-methoxypyridine was obtained (FIG. 3, Step 1).

262 mL of conc. sulfuric acid was cooled down to −2° C., and 262 mL of 90% nitric acid was carefully added thereto. Subsequently, 65.3 g (corresponding to 0.347 mmol) of 2-bromo-3-methoxypyridine was carefully added thereto. After the reaction mixture was stirred in an ice bath for 10 minutes, the mixture was stirred at room temperature for 30 minutes, and then was heated to 55° C. and further stirred for 1.5 hours. After the reaction solution was cooled to room temperature, the reaction solution was poured little by little into crushed ice to generate precipitates. The precipitates were filtered and washed with water, and then dried over phosphorous pentoxide under reduced pressure, to obtain 55.7 g (corresponding to 0.239 mol) of 2-bromo-3-methoxy-6-nitropyridine (FIG. 3, Step 2).

55.6 g (corresponding to 0.239 mol) of 2-bromo-3-methoxy-6-nitropyridine was dissolved in 1700 mL of ethanol, and 37.3 g (50% wet) of 10% palladium-carbon was added thereto under argon stream. To the mixture, 283 mL of hydrazine monohydrate was then added dropwise. After the reaction mixture was heated under reflux for 70 minutes, the reaction solution was cooled down to room temperature. Then, after palladium-carbon was filtered off, the residue was washed with ethanol, and the washings were combined with the filtrate. The combined solution was concentrated under reduced pressure. Then, 1300 mL of water and 130 mL of conc. aqueous ammonia were added to the concentrate, and the resulting mixture was extracted eight times with chloroform. The combined chloroform layers were dried over anhydrous sodium sulfate and concentrated under reduced pressure. The resulting crude product was distilled under reduced pressure to obtain 26.2 g (corresponding to 0.211 mol) of 2-amino-5-methoxypyridine (FIG. 3, Step 3).

4.08 g (corresponding to 30.0 mmol) of 4'-hydroxyacetophenone was dissolved in 250 mL of 28% aqueous ammonium solution, and a solution of 7.61 g (corresponding to 30.0 mmol) of iodine and 24.3 g (corresponding to 146 mmol) of potassium iodide in 60 mL of water was added thereto. The resulting solution was stirred at room temperature for 22.5 hours. After the completion of the reaction, the reaction mixture was concentrated, diluted with water, and then extracted three times with ethyl acetate. The combined ethyl acetate layers were washed once with a saturated sodium chloride solution, dried over anhydrous magnesium sulfate, filtered and concentrated. To the resulting concentrates, 60 mL of water and 40 mL of 8 mol/L sodium hydroxide solution were added, sufficiently mixed, and filtered to remove insoluble matters. Then, conc. hydrochloric acid was added to the filtrate to make it acidic, and the precipitates were filtered and dried under reduced pressure. The resulted precipitates were dissolved in a mixed solution of chloroform and ethyl acetate, and then water was added thereto, and extracted with chloroform for five times. The combined chloroform layers were dried over anhydrous sodium sulfate, and then the solvent was distilled under reduced pressure, to obtain 4.00 g (corresponding to 15.3 mmol) of 4'-hydroxy-3'-iodoacetophenone (FIG. 3, Step 4).

10 mL of ethyl acetate was added to 3.44 g (corresponding to 15.4 mmol) of cupric bromide to obtain a suspension, to which a solution of 2.00 g (corresponding to 7.64 mmol) of 4'-hydroxy-3'-iodoacetophenone in a mixed solution of 18 mL of ethyl acetate and 18 mL of chloroform was added, and the resulting mixture was heated under reflux. After 3.5 hours, the reaction mixture was cooled down to room temperature and filtered. The resulting filtrate was concentrated under reduced pressure. The residue was dissolved in ethyl acetate and subjected to decoloring operation with addition of active charcoal. Then, the resulting solution was filtered and concentrated. The resulting crude product was purified by flash silica gel column chromatography (elution solvent: chloroform/methanol=50/1), to obtain 2.20 g (corresponding to 6.45 mmol) of 2-bromo-4'-hydroxy-3'-iodoacetophenone (FIG. 3, Step 5).

680 mg (corresponding to 1.99 mmol) of 2-bromo-4'-hydroxy-3'-iodoacetophenone and 252 mg (corresponding to 2.03 mmol) of 2-amino-5-methoxypyridine were dissolved in 15 mL of acetonitrile. The resulting solution was heated under reflux in an oil bath at 105° C. for 4 hours. After the completion of the reaction, the reaction solution was cooled down to room temperature, and precipitates were filtered and recovered. The precipitates were washed with acetonitrile and dried under reduced pressure. The resulting crude crystals were suspended in a mixed solution of 5 mL of water and 5 mL of methanol. Then, about 5 mL of a saturated sodium hydrogencarbonate solution was added thereto, and the mixture was sonicated for 5 minutes using an ultrasonic washing machine. Precipitates were filtered and recovered from the resulting mixture, sufficiently washed with water, and dried under reduced pressure, to obtain 435 mg (corresponding to 1.19 mmol) of 2-(4'-hydroxy-3'-iodophenyl)-6-methoxyimidazo[1,2-a]pyridine (FIG. 3, Step 6).

279 mg (corresponding to 0.763 mmol) of 2-(4'-hydroxy-3'-iodophenyl)-6-methoxyimidazo[1,2-a]pyridine that was dissolved in 10 mL of N,N-dimethylformamide, and 317 mg (corresponding to 2.29 mmol) of potassium carbonate was added thereto. The mixture was supplemented with 105 µL (corresponding to 1.15 mmol) of 1-bromo-3-fluoropropane, and then the solution was stirred at room temperature for 21 hours. After the completion of the reaction, the reaction solution was poured into water, and extracted three times with chloroform. The combined chloroform layers were washed with a saturated sodium chloride solution, dried over anhydrous sodium sulfate, filtered and concentrated. The resulting crude product was purified by recycle preparative HPLC (HPLC apparatus: LC-908 (under trade name; manufactured by Japan Analytical Industry Co., Ltd.); column: two JAIGEL 2H (under trade name; manufactured by Japan Analytical Industry Co., Ltd.) connected together; mobile phase: chloroform), to obtain 262 mg (corresponding to 0.614 mmol) of 2-[4'-(3"-fluoropropoxy)-3'-iodophenyl]-6-methoxyimidazo[1,2-a]pyridine (FIG. 1, Step 7).

The NMR measurement results of the resulting 2-[4'-(3"-fluoropropoxy)-3'-iodophenyl]-6-methoxyimidazo[1,2-a]pyridine (internal standard: tetramethylsilane) are shown below.

NMR apparatus employed: JNM-ECP-500 (manufactured by Japan Electron Optics Laboratory Co., Ltd. (JEOL))

$^1$H-NMR (solvent: chloroform-d1; resonance frequency: 500 MHz): δ 8.33 (d, J=2.1 Hz, 1H), 7.85 (dd, J=8.5, 2.1 Hz, 1H), 7.72-7.71 (m, 1H), 7.64-7.62 (m, 1H), 7.51-7.47 (m, 1H), 6.97 (dd, J=9.7, 2.4 Hz, 1H), 6.87 (d, J=8.5 Hz, 1H), 4.75 (dt, $^2J_{HF}$=47.0 Hz, J=5.7 Hz, 2H), 4.19 (t, J=5.7 Hz, 2H), 3.83 (s, 3H), 2.24 (dquint, $^3J_{HF}$=25.7 Hz, J=5.7 Hz, 2H).

$^{19}$F-NMR (solvent: chloroform-d1, resonance frequency: 470 MHz): δ -222.53 (tt, $^2J_{HF}$=47.0 Hz, $^3J_{HF}$=25.7 Hz).

EXAMPLE 4

Synthesis of 2-[3'-tributylstannyl-4'-(3"-fluoropoxy)phenyl]-6-methoxyimidazo[1,2-a]pyridine 107 mg (corresponding to 0.250 mmol) of 2-[4'-(3"-fluoropropoxy)-3'-iodophenyl]-6-methoxyimidazo[1,2-a]pyridine obtained in Example 3 was dissolved in 10 mL of dioxane, and 2 mL of triethylamine was added thereto. Then, 190 µL (corresponding to 0.376 mmol) of bis(tributyltin) and 20 mg (a catalytic amount) of tetrakis-triphenylphosphine palladium were added thereto. After the reaction mixture was stirred at 90° C. for 14.5 hours, the solvent was distilled off under reduced pressure. The residue was purified by silica gel column chromatography (elution solvent: hexane/ethyl acetate=2/1). Further, the resulting crude product was purified by recycle preparative HPLC (HPLC apparatus: LC-908 (under trade name; manufactured by Japan Analytical Industry Co., Ltd.); column: two JAIGEL 2H (under trade name; manufactured by Japan Analytical Industry Co., Ltd.) connected together; mobile phase: chloroform), to obtain 37.8 mg (corresponding to 64.1 µmol) of 2-[3'-tributylstannyl-4'-(3"-fluoropropoxy)phenyl]-6-methoxyimidazo[1,2-a]pyridine (FIG. 4, Step 1).

The NMR measurement results of the resulting 2-[3'-tributylstannyl-4'-(3"-fluoropropoxy)phenyl]-6-methoxyimidazo[1,2-a]pyridine (internal standard: tetramethylsilane) are shown below.

NMR apparatus employed: JNM-ECP-500 (manufactured by Japan Electron Optics Laboratory Co., Ltd. (JEOL))

$^1$H-NMR (solvent: chloroform-d1; resonance frequency: 500 MHz): δ 7.88 (dd, J=8.5, 2.1 Hz, 1H), 7.89-7.78 (m, 1H), 7.73 (s, 1H), 7.66 (d, J=2.3 Hz, 1H), 7.50 (d, J=9.7 Hz, 1H), 6.94 (dd, J=9.7, 2.3 Hz, 1H), 6.91-6.85 (m, 1H), 4.65 (dt, $^2J_{HF}$=47.0 Hz, J=6.0 Hz, 2H), 4.12 (t, J=6.0 Hz, 2H), 3.82 (s, 3H), 2.20 (dquint, $^3J_{HF}$=25.7 Hz, J=6.0, 2H), 1.64-1.45 (m, 6H), 1.33 (sextet, J=7.3 Hz, 6H), 1.16-1.01 (m, 6H), 0.89 (t, J=7.3 Hz, 9H).

$^{13}$C-NMR (solvent: chloroform-d1, resonance frequency: 125 MHz): δ 162.88, 149.20, 145.96, 142.68, 134.64, 130.31, 127.70, 126.84, 119.35, 117.37, 109.64, 108.28, 107.55, 80.81 (d, $^1J_{CF}$=165.1 Hz), 63.53 (d, $^3J_{CF}$=5.8 Hz), 56.20, 30.63 (d, $^2J_{CF}$=20.2 Hz), 29.16, 27.35, 13.67, 9.90.

$^{19}$F-NMR (solvent: chloroform-d1, resonance frequency: 470 MHz): δ −221.43 (tt, $^2J_{HF}$=47.0 Hz, $^3J_{HF}$=25.7 Hz).

EXAMPLE 5

Synthesis of 2-[4'-(2"-fluoroethoxy)-3'-iodophenyl]-6-methoxyimidazo[1,2-a]pyridine (non-radioactive iodinated form)

1.46 g (corresponding to 4.28 mmol) of 2-bromo-4'-hydroxy-3'-iodoacetophenone and 584 mg (corresponding to 4.71 mmol) of 2-amino-5-methoxypyridine were dissolved in 30 mL of acetonitrile. The resulting solution was heated under reflux in an oil bath at 110° C. for 2.5 hours. After the completion of the reaction, the reaction solution was cooled down to room temperature, and precipitates were filtered and recovered. The precipitates were washed with acetonitrile and dried under reduced pressure. The resulting crude crystals were suspended in a mixed solution of 3.0 mL of water and 1.0 mL of methanol. Then, about 10 mL of a saturated sodium hydrogencarbonate solution was added thereto, and the mixture was sonicated for 5 minutes using an ultrasonic washing machine. Precipitates were filtered and recovered from the resulting mixture, sufficiently washed with water, and dried under reduced pressure, to obtain 812 mg (corresponding to 2.22 mmol) of 2-(4'-hydroxy-3'-iodophenyl)-6-methoxyimidazo[1,2-a]pyridine (FIG. 5, Step 1).

366 mg (corresponding to 1.00 mmol) of 2-(4'-hydroxy-3'-iodophenyl)-6-methoxyimidazo[1,2-a]pyridine that was sufficiently dried to remove moisture was dissolved in 10.0 mL of N,N-dimethylformamide, and 415 mg (corresponding to 3.00 mmol) of potassium carbonate was added thereto. The mixture was supplemented with 327 mg (corresponding to 1.50 mmol) of 1-fluoro-2-paratoluenesulfonyloxyethane, and then the solution was stirred at 90° C. for 2 hours. After the completion of the reaction, a saturated aqueous ammonium chloride solution was added thereto, and extracted three times with ethyl acetate. The combined ethyl acetate layers were washed with water and a saturated sodium chloride solution, dried over anhydrous sodium sulfate, and concentrated under reduced pressure. The resulting crude product was purified by silica gel column chromatography (elution solvent: hexane/ethyl acetate=½), to obtain 381 mg (corresponding to 0.924 mmol) of 2-[4'-(2"-fluoroethoxy)-3'-iodophenyl]-6-methoxyimidazo[1,2-a]pyridine (FIG. 5, Step 2).

The NMR measurement results of the resulting 2-[4'-(2"-fluoroethoxy)-3'-iodophenyl]-6-methoxyimidazo[1,2-a]pyridine (internal standard: tetramethylsilane) are shown below.

NMR apparatus employed: JNM-ECP-500 (manufactured by Japan Electron Optics Laboratory Co., Ltd. (JEOL))

$^1$H-NMR (solvent: chloroform-d1; resonance frequency: 500 MHz): δ 8.34 (d, J=1.8 Hz, 1H), 7.87 (dd, J=1.8, 8.7 Hz, 1H), 7.73 (s, 1H), 7.64 (d, J=2.3 Hz, 1H), 7.50 (d, J=9.6 Hz, 1H), 6.98 (dd, J=1.8, 9.6 Hz, 1H), 6.89 (d, J=8.7 Hz, 1H), 4.82 (dt, $^2J_{HF}$=47.2 Hz, J=4.1 Hz, 2H), 4.31 (dt, $^3J_{HF}$=27.0 Hz, J=4.1 Hz, 2H), 3.83 (s, 3H).

EXAMPLE 6

Synthesis of 2-[3'-tributylstannyl-4'-(2"-fluoroethoxy)phenyl]-6-methoxyimidazo[1,2-a]pyridine 297 mg (corresponding to 0.721 mmol) of 2-[4'-(2"-fluoroethoxy)-3'-iodophenyl]-6-methoxyimidazo[1,2-a]pyridine obtained in Example 5 was dissolved in 7.0 mL of dioxane, and 3.0 mL of triethylamine was added thereto. Then, 0.55 mL (corresponding to 1.1 mmol) of bis(tributyltin) and 55.0 mg (a catalytic amount) of tetrakis-triphenylphosphine palladium were added thereto. After the reaction mixture was stirred at 90° C. for 18 hours, the solvent was distilled off under reduced pressure. The residue was purified by flash silica gel column chromatography (elution solvent: hexane/ethyl acetate=2/1), to obtain 188 mg (corresponding to 0.327 mmol) of 2-[3'-tributylstannyl-4'-(2"-fluoroethoxy)phenyl]-6-methoxyimidazo[1,2-a]pyridine (FIG. 6, Step 1).

The NMR measurement results of the resulting 2-[3'-tributylstannyl-4'-(2"-fluoroethoxy)phenyl]-6-methoxyimidazo[1,2-a]pyridine (internal standard: tetramethylsilane) are shown below.

NMR apparatus employed: JNM-ECP-500 (manufactured by Japan Electron Optics Laboratory Co., Ltd. (JEOL))

$^1$H-NMR (solvent: chloroform-d1; resonance frequency: 500 MHz): δ 7.89 (dd, J=2.3, 8.7 Hz, 1H), 7.84 (d, J=2.3 Hz, 1H), 7.73 (s, 1H), 7.66 (s, 1H), 7.51 (d, J=9.6 Hz, 1H), 6.95 (d, J=9.6 Hz, 1H), 6.84 (d, J=8.7 Hz, 1H), 4.73 (dt, $^2J_{HF}$=46.7 Hz, J=3.7 Hz, 2H), 4.22 (dt, $^3J_{HF}$=23.8 Hz, J=3.7 Hz, 2H), 3.82 (s, 3H), 1.58-1.51 (m, 6H), 1.37-1.30 (m, 6H), 1.13-1.06 (m, 6H), 0.89 (t, J=7.3 Hz, 9H).

EXAMPLE 7

Synthesis of 2-[4'-(2"-hydroxyethoxy)-2'-methoxyphenyl]-6-iodoimidazo[1,2-a]pyridine (non-radioactive iodinated form)

2.50 g (corresponding to 20.0 mmol) of 2-bromoethanol and 2.72 g (corresponding to 40.0 mmol) of imidazole were dissolved in 10 mL of N,N-dimethylformamide (DMF), and cooled to 0° C. Then, 5.50 g (corresponding to 20.0 mmol) of t-butyldiphenylchlorosilane (TBDPSCl) was added thereto. After the reaction mixture was stirred at room temperature for 18 hours, a saturated aqueous sodium chloride solution was added, and extracted three times with ethyl acetate. The combined ethyl acetate layers were dried over anhydrous sodium sulfate, and concentrated under reduced pressure. The resulting crude product was purified by silica gel column chromatography (elution solvent: hexane/ethyl acetate=10/1) to obtain 7.04 g (corresponding to 19.4 mmol) of 1-bromo-2-(t-butyldiphenylsiloxy)ethane (FIG. 7, Step 1).

1.00 g (corresponding to 6.57 mmol) of 2',4'-dihydroxyacetophenone was dissolved in 30.0 mL of dimethylformamide, and 908 mg (corresponding to 7.88 mmol) of potassium carbonate was added thereto. Then, 2.39 g (corresponding to 6.57 mmol) of 1-bromo-2-(t-butyldiphenylsiloxy)ethane was added thereto. After the reaction mixture was stirred at 90° C. for 2 hours, a saturated aqueous ammonium chloride solution was added, and extracted three times with ethyl acetate. The combined ethyl acetate layers were dried over anhydrous sodium sulfate, and concentrated under reduced pressure. The resulting crude product was purified by silica gel column chromatography (elution solvent: hexane/ethyl acetate=10/1) to obtain 2.11 g (corresponding to 4.86 mmol) of 4'-(2"-t-butyldiphenylsiloxyethoxy)-2'-hydroxyacetophenone (FIG. 7, Step 2).

175 mg (corresponding to 7.29 mmol) of sodium hydroxide was suspended in 30 mL of tetrahydrofuran, and 2.11 g (corresponding to 4.86 mmol) of 4'-(2"-t-butyldiphenylsiloxyethoxy)-2'-hydroxyacetophenone was added thereto. After the reaction mixture was stirred at room temperature for 10 minutes, 0.454 mL (corresponding to 4.86 mmol) of iodomethane was added thereto, and further stirred at 90° C. for 4 hours. After the completion of the reaction, a saturated aqueous ammonium chloride solution was added, and extracted for three times with ethyl acetate. The combined ethyl acetate layers were dried over anhydrous magnesium sulfate, and concentrated under reduced pressure. The resulting crude product was purified by silica gel column chromatography (elution solvent: hexane/ethyl acetate=10/1), to obtain 1.25 g (corresponding to 4.86 mmol) of 4'-(2"-t-butyldiphenylsiloxyethoxy)-2'-methoxyacetophenone (FIG. 7, Step 3).

13 mL of ethyl acetate was added to 1.31 g (corresponding to 5.86 mmol) of cupric bromide to obtain a suspension, to which 1.25 g (corresponding to 4.86 mmol) of 4'-(2"-t-butyldiphenylsiloxyethoxy)-2'-methoxyacetophenone was added. Then, the resulting mixture was heated under reflux. After 3 hours, the reaction mixture was cooled down to room temperature and filtered. The resulting filtrate was concentrated under reduced pressure. The residue was dissolved in ethyl acetate and subjected to decoloring operation with addition of active charcoal. Then, the resulting solution was filtered and concentrated. The resulting crude product was purified by flash silica gel column chromatography (elution solvent: hexane/ethyl acetate=10/1) to obtain 666 mg (corresponding to 1.26 mmol) of 2-bromo-4'-(2"-t-butyldiphenylsiloxyethoxy)-2'-methoxyacetophenone (FIG. 7, Step 4).

666 mg (corresponding to 1.26 mmol) of 2-bromo-4'-(2"-t-butyldiphenylsiloxyethoxy)-2'-methoxyacetophenone and 360 mg (corresponding to 1.64 mmol) of 2-amino-5-iodopyridine were dissolved in 5.0 mL of acetonitrile. The resulting solution was heated under reflux in an oil bath at 110° C. for 2 hours. After the completion of the reaction, the reaction solution was cooled down to room temperature, and precipitates were filtered and recovered. The precipitates were washed with acetonitrile and dried under reduced pressure, to obtain 525 mg (corresponding to 0.720 mmol) of 2-[4'-(2"-t-butyldiphenylsiloxyethoxy)-2'-methoxyphenyl]-6-iodoimidazo[1,2-a]pyridine.hydrogenbromide (FIG. 7, Step 5).

200 mg (corresponding to 0.274 mmol) of 2-[4'-(2"-t-butyldiphenylsiloxyethoxy)-2'-methoxyphenyl]-6-iodoimidazo[1,2-a]pyridine was dissolved in 2.0 mL of tetrahydrofuran, and 0.33 mL of a 1.0 mol/L tetrahydrofuran solution of tetrabutylammoniumfluoride was added thereto. After the reaction mixture was stirred at room temperature for 4 hours, an aqueous sodium hydrogencarbonate solution was added followed by addition of 5.0 mL of water and 1.0 mL of acetonitrile to filter precipitates. The filtered precipitates were washed with water and acetonitrile in this order to obtain 103 mg (corresponding to 0.251 mmol) of 2-[4'-(2"-hydroxyethoxy)-2'-methoxyphenyl]-6-iodoimidazo[1,2-a]pyridine (FIG. 7, Step 6).

The NMR measurement results of the resulting 2-[4'-(2"-hydroxyethoxy)-2'-methoxyphenyl]-6-iodoimidazo[1,2-a]pyridine (internal standard: tetramethylsilane) are shown below.

NMR apparatus employed: JNM-ECP-500 (manufactured by Japan Electron Optics Laboratory Co., Ltd. (JEOL))

$^1$H-NMR (solvent: dimethylformamide-d6; resonance frequency: 500 MHz): δ 8.92 (s, 1H), 8.24 (s, 1H), 8.16 (d, J=8.7 Hz, 1H), 7.38 (s, 2H), 6.69 (d, J=1.8 Hz, 1H), 6.65 (dd, J=8.7, 1.8 Hz, 1H), 4.89 (brs, 1H), 4.06-4.04 (m, 2H), 4.13 (s, 3H), 3.73-3.75 (m, 2H).

EXAMPLE 8

Synthesis of 6-tributylstannyl-2-[4'-(2"-hydroxyethoxy)-2'-methoxyphenyl]imidazo[1,2-a]pyridine 30 mg (corresponding to 0.073 mmol) of 2-[4'-(2"-hydroxyethoxy)-2'-methoxyphenyl]-6-iodoimidazo[1,2-a]pyridine obtained in Example 7 was dissolved in 2.0 mL of dioxane, and 1.0 mL of triethylamine was added thereto. Then, 0.060 mL (corresponding to 0.11 mmol) of bis(tributyltin) and 5.1 mg (a catalytic amount) of tetrakis-triphenylphosphine palladium were added thereto. After the reaction mixture was stirred at 90° C. for 23 hours, the solvent was distilled off under reduced pressure. The residue was purified by flash silica gel column chromatography (elution solvent: hexane/ethyl acetate=1/2) to obtain 24.0 mg (corresponding to 0.0419 mmol) of 6-tributylstannyl-2-[4'-(2"-hydroxyethoxy)-2'-methoxyphenyl]imidazo[1,2-a]pyridine (FIG. 8, Step 1).

The NMR measurement results of the resulting 6-tributylstannyl-2-[4'-(2"-hydroxyethoxy)-2'-methoxyphenyl]imidazo[1,2-a]pyridine (internal standard: tetramethylsilane) are shown below.

NMR apparatus employed: JNM-ECP-500 (manufactured by Japan Electron Optics Laboratory Co., Ltd. (JEOL))

$^1$H-NMR (solvent: chloroform-d1; resonance frequency: 500 MHz): δ 8.23 (d, J=8.7 Hz, 1H), 8.06 (s, 1H), 7.98 (s, 1H), 7.58 (d, J=8.2 Hz, 1H), 7.13 (d, J=8.7 Hz, 1H), 6.64-6.60 (m, 2H), 4.15 (t, J=4.6 Hz, 2H), 4.00-3.98 (m, 5H), 1.64-1.48 (m, 6H), 1.38-1.31 (m, 6H), 1.18-1.04 (m, 6H), 0.90 (t, J=7.3 Hz, 9H).

$^{13}$C-NMR (solvent: chloroform-d1, resonance frequency: 125 MHz): δ 159.4, 157.8, 144.3, 140.5, 131.0, 130.1, 129.7, 121.3, 116.6, 116.1, 110.5, 105.6, 99.3, 69.4, 61.5, 55.5, 29.0, 27.3, 13.7, 9.8.

EXAMPLE 9

Synthesis of 2-[4'-(2"-hydroxyethoxy)-2'-methoxyphenyl]-6-[$^{123}$I]iodoimidazo[1,2-a]pyridine To 60 µL of a solution in methanol of 6-tributylstannyl-2-[4'-(2"-hydroxyethoxy)-2'-methoxyphenyl]imidazo[1,2-a]pyridine (concentration: 1 mg/mL), 40 µL of 2 mol/L hydrochloric acid, 40 µL of [$^{123}$I]sodium iodide of 135.7 MBq and 20 µL of 10% (w/v) hydrogen peroxide were added. After the mixed solution was left to stand at 50° C. for 10 minutes, it was subjected to HPLC under the following conditions to obtain a fraction of 2-[4'-(2"-hydroxyethoxy)-2'-methoxyphenyl]-6-[$^{123}$I]iodoimidazo[1,2-a]pyridine.

HPLC Conditions:
Column: Phenomenex Luna C18 (trade name; manufactured by Phenomenex Co.; size: 4.6×150 mm)
Mobile phase: 0.1% trifluoroacetic acid in water/0.1% trifluoroacetic acid in acetonitrile=80/20 to 0/100 (17 minutes)
Flow rate: 1.0 mL/min.
Detector: Ultraviolet visible absorptiometer (Detection wavelength: 282 nm) and radioactivity counter (manufactured by raytest: type STEFFI)

10 ml of water was added to the fraction. The resulting solution was passed through a reversed phase column (trade name: Sep-Pak (registered trademark) Light C8 Cartridges manufactured by Waters: the packed amount of the packing agent: 145 mg) so that the column adsorbs and collects 2-[4'-(2"-hydroxyethoxy)-2'-methoxyphenyl]-6-[$^{123}$I]iodoimidazo[1,2-a]pyridine. The column was rinsed with 1 mL of water, and then 1 mL of diethyl ether was passed therethrough to elute 2-[4'-(2"-hydroxyethoxy)-2'-methoxyphenyl]-6-[$^{123}$I]iodoimidazo[1,2-a]pyridine. The amount of radioactivity of the obtained compound was 55.7 MBq at the end of synthesis. Further, the TLC analysis was conducted under the following conditions, and as a result, the radiochemical purity of the compound was 99%.

TLC Analysis Conditions:
TLC plate: Silica Gel 60 $F_{254}$ (trade name; manufactured by Merck & Co., Inc.)
Mobile phase: Chloroform/methanol/triethylamine=100/1/2
Detector: Rita Star (trade name; manufactured by raytest)

EXAMPLE 10

Synthesis of 6-tributylstannyl-2-[4'-(2"-hydroxyethoxy)phenyl]-7-methylimidazo[1,2-a]pyridine 50 mL of ethyl acetate was added to 28.17 g (corresponding to 126 mmol) of cupric bromide to obtain a suspension, to which a solution of 8.18 g (corresponding to 60.0 mmol) of 4'-hydroxyacetophenone in a mixed solution of 50 mL of ethyl acetate and 50 mL of chloroform was added. Then, the resulting mixture was heated under reflux. After 5 hours, the reaction mixture was cooled down to room temperature and filtered. The resulting filtrate was concentrated under reduced pressure. The residue was dissolved in ethyl acetate and subjected to decoloring operation with addition of active charcoal. Then, the resulting solution was filtered and concentrated. The resulting crude product was purified by flash silica gel column chromatography (elution solvent: chloroform/methanol=20/1), and recrystallized from ethyl acetate/petroleum ether, to obtain 7.25 g (corresponding to 33.7 mmol) of 2-bromo-4'-hydroxyacetophenone (FIG. 9, Step 1).

2.00 g (corresponding to 9.28 mmol) of 2-bromo-4'-hydroxyacetophenone and 1.91 g (corresponding to 10.2 mmol) of 2-amino-5-bromo-4-methylpyridine were dissolved in 40 mL of acetonitrile. The resulting solution was heated under reflux in an oil bath at 110° C. for 3 hours. After the completion of the reaction, the reaction solution was cooled down to room temperature, and precipitates were filtered and recovered. The precipitates were washed with acetonitrile and dried under reduced pressure. The resulting crude crystals were suspended in a mixed solution of 10 mL of water and 10 mL of methanol. Then, about 50 mL of a saturated sodium hydrogencarbonate solution was added thereto, and the mixture was sonicated for 10 minutes using an ultrasonic washing machine. Precipitates were filtered and recovered from the resulting mixture, sufficiently washed with water, and dried under reduced pressure, to obtain 2.67 g (corresponding to 8.81 mmol) of 6-bromo-2-[4'-hydroxyphenyl]-7-methylimidazo[1,2-a]pyridine (FIG. 9, Step 2).

10.0 g (corresponding to 80.0 mmol) of 2-bromoethanol and 10.9 g (corresponding to 160 mmol) of imidazole were dissolved in 100 mL of N,N-dimethylformamide (DMF), and cooled to 0° C. Then, 12.1 g (corresponding to 80.0 mmol) of t-butyldimethylchlorosilane (TBDMSCl) was added thereto. After the reaction mixture was stirred at room temperature for 3 hours, a saturated aqueous sodium hydrogencarbonate solution was added, and extracted three times with ethyl acetate. The combined ethyl acetate layers were dried over anhydrous sodium sulfate, and concentrated under reduced pressure. The resulting crude product was purified by distillation under reduced pressure (120° C., 100 mmHg), to obtain 14.5 g (corresponding to 60.6 mmol) of 1-bromo-2-(t-butyldimethylsiloxy)ethane (FIG. 9, Step 3).

462 mg (corresponding to 1.52 mmol) of 6-bromo-2-(4'-hydroxyphenyl)-7-methylimidazo[1,2-a]pyridine was dissolved in 10 mL of dimethylformamide, and 630 mg (corresponding to 4.56 mmol) of potassium carbonate was added thereto. Then, 400 mg (corresponding to 1.67 mmol) of 1-bromo-2-(t-butyldimethylsiloxy)ethane was added thereto. After the reaction mixture was stirred at room temperature for 4 days, a saturated aqueous sodium chloride solution was added, and extracted three times with ethyl acetate. The combined ethyl acetate layers were dried over anhydrous sodium sulfate, and concentrated under reduced pressure. The resulting crude product was purified by silica gel column chromatography (ethyl acetate) to obtain 571 mg (corresponding to 1.24 mmol) of 6-bromo-2-[4'-(2"-t-butyldimethylsiloxyethoxy)phenyl]-7-methylimidazo[1,2-a]pyridine (FIG. 9, Step 4).

571 mg (corresponding to 1.24 mmol) of 6-bromo-2-[4'-(2"-t-butyldimethylsiloxyethoxy)phenyl]-7-methylimidazo[1,2-a]pyridine was dissolved in 3.0 mL of tetrahydrofuran, and 1.24 mL of a 1.0 mol/L solution in tetrahydrofuran of tetrabutylammoniumfluoride was added thereto. After the reaction mixture was stirred at room temperature for 20 minutes, an aqueous ammonium chloride solution was added, and extracted three times with ethyl acetate. The combined ethyl acetate layers were dried over anhydrous sodium sulfate, and concentrated under reduced pressure. The resulting crude product was washed with water and ethyl acetate, to obtain 320 mg (corresponding to 0.922 mmol) of 6-bromo-2-[4'-(2"-hydroxyethoxy)phenyl]-7-methylimidazo[1,2-a]pyridine (FIG. 9, Step 5).

100 mg (corresponding to 0.288 mmol) of 6-bromo-2-[4'-(2"-hydroxyethoxy)phenyl]-7-methylimidazo[1,2-a]pyridine was dissolved in 4.0 mL of dioxane, and 2.0 mL of triethylamine was added thereto. Then, 0.22 mL (corresponding to 0.43 mmol) of bis(tributyltin) and 22.0 mg (a catalytic amount) of tetrakis-triphenylphosphine palladium were added thereto. After the reaction mixture was stirred at 90° C. for 17 hours, the solvent was distilled off under reduced pressure. The residue was purified by flash silica gel column chromatography (elution solvent: hexane/ethyl acetate=1/2), to obtain 63.8 mg (corresponding to 0.114 mmol) of 6-tributylstannyl-2-[4'-(2"-hydroxyethoxy)phenyl]-7-methylimidazo[1,2-a]pyridine (FIG. 9, Step 6).

The NMR measurement results of the resulting 6-tributylstannyl-2-[4'-(2"-hydroxyethoxy)phenyl]-7-methylimidazo[1,2-a]pyridine (internal standard: tetramethylsilane) are shown below.

NMR apparatus employed: JNM-ECP-500 (manufactured by Japan Electron Optics Laboratory Co., Ltd. (JEOL))

$^1$H-NMR (solvent: chloroform-d1; resonance frequency: 500 MHz): δ 7.87 (d, J=8.7 Hz, 2H), 7.67 (s, 1H), 7.38 (s, 1H), 6.98 (d, J=8.7 Hz, 2H), 4.13 (t, J=4.5 Hz, 2H), 3.98 (t, J=4.5 Hz, 2H), 2.39 (s, 3H), 1.60-1.46 (m, 6H), 1.39-1.32 (m, 6H), 1.20-1.06 (m, 6H), 0.91 (t, J=7.3 Hz, 9H)

EXAMPLE 11

Synthesis of 2-[4'-(2"-hydroxyethoxy)phenyl]-6-[$^{123}$I]iodo-7-methylimidazo[1,2-a]pyridine To 60 μL of a solution of 6-tributylstannyl-2-[4'-(2"-hydroxyethoxy)phenyl]-7-methylimidazo[1,2-a]pyridine in methanol (concentration: 1 mg/mL), 60 μL of 1 mol/L hydrochloric acid, 20 μL of 1 mmol/L sodium iodide, 50 μL of [$^{123}$I]sodium iodide of 560 MBq and 20 μL of 10% (w/v) hydrogen peroxide were added. After the mixed solution was left to stand at 50° C. for 10 minutes, it was subjected to HPLC under the same conditions as in Example 9 to obtain a fraction of 2-[4'-(2"-hydroxyethoxy)phenyl]-6-[$^{123}$I]iodo-7-methylimidazo[1,2-a]pyridine.

10 ml of water was added to the fraction. The resulting solution was passed through a reversed phase column (trade name: Sep-Pak (registered trademark) Light C8 Cartridges manufactured by Waters: the packed amount of the packing agent: 145 mg) so that the column adsorbs and collects 2-[4'-(2"-hydroxyethoxy)phenyl]-6-[$^{123}$I]iodo-7-methylimidazo[1,2-a]pyridine. The column was rinsed with 1 mL of water, and then 1 mL of diethyl ether was passed therethrough to elute 2-[4'-(2"-hydroxyethoxy)phenyl]-6-[$^{123}$I]iodo-7-methylimidazo[1,2-a]pyridine. The amount of radioactivity of the obtained compound was 22 MBq at the end of synthesis. Further, the TLC analysis was conducted under the same conditions as in Example 9, and as a result, the radiochemical purity of the compound was 98%.

REFERENCE EXAMPLE 1

Synthesis of [$^{123}$I]-IMPY

[$^{123}$I]-IMPY was synthesized in accordance with the following steps for use in Comparative Examples for evaluations on measurement of log $P_{octanol}$.

In accordance with the method described in a literature (Zhi-Ping Zhuang et al., J. Med. Chem, 2003, 46, p. 237-243), 6-tributylstannyl-2-[4'-(N,N-dimethylamino)phenyl]imidazo[1,2-a]pyridine was synthesized, and dissolved in methanol (concentration: 1 mg/mL). To 53 μL of the resulting solution, 75 μL of 1 mol/L hydrochloric acid, 60-70 μL of [$^{123}$I]sodium iodide of 224-253 MBq, 10 μL of a 1 mmol/L sodium iodide solution and 15 μL of 10% (w/v) hydrogen peroxide were added. After the mixed solution was left to stand at 50° C. for 10 minutes, the solution was subjected to HPLC under the same conditions as described in Example 3, to obtain a fraction of [$^{123}$I]-IMPY.

10 ml of water was added to the fraction. The resulting solution was passed through a reversed phase column (trade name: Sep-Pak (registered trademark) Light C8 Cartridges manufactured by Waters; the packed amount of the packing agent: 145 mg), so that the column adsorbs and collects the [$^{123}$I]-IMPY. The column was rinsed with 1 mL of water, and then 1 mL of diethyl ether was passed therethrough, to elute [$^{123}$I]-IMPY. The obtained radioactivity was 41-57 MBq at the end of synthesis. Further, the TLC analysis was conducted under the same conditions as described in Example 9, and as a result, the radiochemical purity of the compound was 93%.

EXAMPLE 12

Synthesis of 2-[4'-(3"-fluoropropoxy)-3'-[$^{123}$I]iodophenyl]-6-methoxyimidazo[1,2-a]pyridine To 50 μL of a solution of 2-[3'-tributylstannyl-4'-(3"-fluoropropoxy)phenyl]-6-methoxyimidazo[1,2-a]pyridine (concentration: 1 mg/mL) in a mixed solution of methanol/dimethylsulfoxide (mixing ratio: 9/1), 50 μL of 1 mol/L hydrochloric acid, 10 μL of 1 mmol/L sodium iodide, 50 μL of [$^{123}$I]sodium iodide of 356 MBq and 10 μL of 10% (w/v) hydrogen peroxide were added. After the mixed solution was left to stand at 50° C. for 10 minutes, it was subjected to HPLC under the same conditions as in Example 9 to obtain a fraction of 2-[4'-(3"-fluoropropoxy)-3'-[$^{123}$I]iodophenyl]-6-methoxyimidazo[1,2-a]pyridine.

10 ml of water was added to the fraction. The resulting solution was passed through a reversed phase column (trade name: Sep-Pak (registered trademark) Light C8 Cartridges manufactured by Waters; the packed amount of the packing agent: 130 mg), so that the column adsorbs and collects 2-[4'-(3"-fluoropropoxy)-3'-[$^{123}$I]iodophenyl]-6-methoxyimidazo[1,2-a]pyridine. The column was rinsed with 1 mL of water, and then 1 mL of diethyl ether was passed therethrough, to elute 2-[4'-(3"-fluoropropoxy)-3'-[$^{123}$I]iodophenyl]-6-methoxyimidazo[1,2-a]pyridine. The obtained radioactivity was 261.6 MBq at the end of synthesis. Further, the TLC analysis was conducted under the following conditions, and as a result, the radiochemical purity of the compound was 98%.

TLC Analysis Conditions:
TLC plate: Silica Gel 60 F$_{254}$ (trade name; manufactured by Merck & Co., Inc.)
Mobile phase: Chloroform/methanol/triethylamine=100/1/2
Detector: Bio-imaging Analyzer (type: BAS-2500; manufactured by FUJIFILM Corporation)

EXAMPLE 13

Synthesis of 2-[4'-(2"-fluoroethoxy)-3'-methoxyphenyl]-6-[$^{123}$I]iodoimidazo[1,2-a]pyridine To 70 μL of a solution of 6-tributylstannyl-2-[4'-(2"-fluoroethoxy)-3'-methoxyphenyl]imidazo[1,2-a]pyridine (concentration: 1 mg/mL) in a mixed solution of methanol/dimethylsulfoxide (in a ratio of 9/1), 50 μL of 2 mol/L hydrochloric acid, 15 μL of 1 mmol/L sodium iodide, 80 μL of [$^{123}$I]sodium iodide of 309 MBq and 15 μL of 10% (w/v) hydrogen peroxide were added. After the mixed solution was left to stand at 50° C. for 10 minutes, the solution was subjected to HPLC under the same conditions as in Example 9, to obtain a fraction of 2-[4'-(2"-fluoroethoxy)-3'-methoxyphenyl]-6-[$^{123}$I]iodoimidazo[1,2-a]pyridine.

10 ml of water was added to the fraction. The resulting solution was passed through a reversed phase column (trade name: Sep-Pak (registered trademark) Light C8 Cartridges manufactured by Waters: the packed amount of the packing agent: 145 mg) so that the column adsorbs and collects 2-[4'-(2"-fluoroethoxy)-3'-methoxyphenyl]-6-[$^{123}$I]iodoimidazo[1,2-a]pyridine. The column was rinsed with 1 mL of water, and then 1 mL of diethyl ether was passed therethrough to elute 2-[4'-(2"-fluoroethoxy)-3'-methoxyphenyl]-6-[$^{123}$I]iodoimidazo[1,2-a]pyridine. The amount of radioactivity of the obtained compound was 98.4 MBq at the end of synthesis. Further, the TLC analysis was conducted under the same conditions as in Example 12, and as a result, the radiochemical purity of the compound was 92%.

EXAMPLE 14

Synthesis of 2-[4'-(2"-fluoroethoxy)-3'-[$^{123}$I]iodophenyl]-6-methoxyimidazo[1,2-a]pyridine To 75 μL of a solution of 2-[3'-tributylstannyl-4'-(2"-fluoroethoxy)phenyl]-6-methoxyimidazo[1,2-a]pyridine (concentration: 1 mg/mL) in a mixed solution of methanol/dimethylsulfoxide (in a ratio of 9/1), 150 μL of 2 mol/L hydrochloric acid, 15 μL of 1 mmol/L sodium iodide, 200 μL of [$^{123}$I]sodium iodide of 204 MBq and 15 μL of 10% (w/v) hydrogen peroxide were added. After the mixed solution was left to stand at 50° C. for 10 minutes, the solution was subjected to HPLC under the same conditions as in Example 9, to obtain a fraction of 2-[4'-(2"-fluoroethoxy)-3'-[$^{123}$I]iodophenyl]-6-methoxyimidazo[1,2-a]pyridine.

10 ml of water was added to the fraction. The resulting solution was passed through a reversed phase column (trade name: Sep-Pak (registered trademark) Light C8 Cartridges manufactured by Waters: the packed amount of the packing agent: 145 mg) so that the column adsorbs and collects 2-[4'-(2"-fluoroethoxy)-3'-[$^{123}$I]iodophenyl]-6-methoxyimidazo[1,2-a]pyridine. The column was rinsed with 1 mL of water, and then 1 mL of diethyl ether was passed therethrough to elute 2-[4'-(2"-fluoroethoxy)-3'-[$^{123}$I]iodophenyl]-6-methoxyimidazo[1,2-a]pyridine. The amount of radioactivity of the obtained compound was 89.0 MBq at the end of synthesis. Further, the TLC analysis was conducted under the same conditions as in Example 12, and as a result, the radiochemical purity of the compound was 99%.

EXAMPLES 15 TO 17, COMPARATIVE EXAMPLE 1

Measurement of Partition Coefficient Based on the Octanol Extraction Method

Partition coefficients based on the octanol extraction method (hereinafter referred to as log $P_{octanol}$) were measured, which are generally known as an indicator of permeability of compounds through the blood-brain barrier (hereinafter referred to as BBB).

Method

Each diethyl ether solution of Compound 1 (Example 15), Compound 2 (Example 16), Compound 3 (Example 17), Compound 4 (Example 18) and [$^{123}$I]-IMPY (Comparative Example 1) was each diluted with 10 mg/mL ascorbic acid-containing physiological saline solution, and adjusted to a radioactive concentration of 20-30 MBq/mL. To 2 mL of octanol, 10 μL each of the solutions was added, and 2 mL of 10 mmol/L phosphate buffer (pH 7.4) was added, followed by stirring for 30 seconds. After each mixture was centrifuged (2000 rpm×60 min.) with a low-speed centrifuge (type: CTD4, manufactured by Hitachi Koki, Co., Ltd.), the octanol layer and the water layer were sampled each in an amount of 1 mL, and subjected to measurement of radioactivity count with an autowell gamma system (Type: ARC-301B, manufactured by Aloka). Using the obtained radioactivity count, log $P_{octanol}$ was calculated in accordance with the equation (1).

$$\log P_{octanol} = \log_{10}\left(\frac{\text{Radioactivity count of octanol layer}}{\text{Radioactivity count of water layer}}\right) \quad (1)$$

Results

The results are shown in Table 2. As shown in the Table, all the compounds showed log $P_{octanol}$ values between 1 and 3. It is known that compounds permeable to BBB show a log $P_{octanol}$ value between 1 and 3 (Douglas D. Dischino et al., J. Nucl. Med., (1983), 24, p. 1030-1038). From the above results, it is implied that Compounds 1, 2 and 3 have a BBB permeability like IMPY.

TABLE 2 log$P_{octanol}$ value of the present compound

| Experiment | Compound | log$P_{octanol}$ value |
|---|---|---|
| Comparative Example 1 | [$^{123}$I]-IMPY | 1.9 |
| Example 15 | Compound 1 | 2.3 |
| Example 16 | Compound 2 | 1.8 |
| Example 17 | Compound 3 | 2.6 |
| Example 18 | Compound 4 | 2.7 |

EXAMPLES 19 TO 22, COMPARATIVE EXAMPLE 2

Measurement of Transferability into Brain and Clearance

Using Compounds 1, 2 and 3, a time course change of radioactive accumulation in brain of male Wistar rats (7-week old) was measured.

Method

Compound 1 in 10 mg/mL ascorbic acid-containing physiological saline solution (24 MBq/mL in radioactive concentration), Compound 2 in 10 mg/mL ascorbic acid-containing physiological saline solution (30 MBq/mL in radioactive concentration), Compound 4 in 10 mg/mL ascorbic acid-containing physiological saline solution (32 MBq/mL in radioactive concentration) and Compound 3 in 10 mg/mL ascorbic acid-containing physiological saline solution (30 MBq/mL in radioactive concentration) were prepared to obtain sample solutions. The sample solutions were injected under thiopental anesthesia into the tail vein of the male Wistar rats (7-week old) (dosage: 0.05 mL, dosed radioactivity: 1.2-1.5 MBq equivalent). The rats were sacrificed by bleeding from abdominal artery, and brains were removed and subjected to measurement of mass of brains and further subjected to measurement of radioactivity (hereinafter referred to as A in this Example) with a single channel analyzer (detector type: SP-20 manufactured by OHYO KOKEN KOGYO Co., Ltd.) 2, 5, 30 and 60 minutes after the injection. Further, the radioactivity level of the rest of the whole body was measured in the same manner as above (hereinafter referred to as B in this Example). Using these measurement results, radioactive accumulation per unit weight of brain (% ID/g) at the respective time points of dissection was calculated in accordance with the following formula (2) (Examples 19 to 22).

Separately, [$^{123}$I]-IMPY in 10 mg/mL ascorbic acid-containing physiological saline solution (20-30 MBq/mL in radioactive concentration) was prepared, the same operation as above was conducted, and radioactive accumulation per unit weight of brain (% ID/g) at the respective time points of dissection was calculated (Comparative Example 2).

Meanwhile, three animals were used for Examples 19 to 22 and Comparative Example 2 at the respective time points.

$$\% \ ID/g = \frac{A}{B \times \text{brain weight}} \times 100 \qquad (2)$$

Results

The results are shown in Table 3. As shown in Table 3, Compounds 1, 2, 3 and 4 showed a significant radioactive accumulation like [$^{123}$I]-IMPY at the time point of two minutes after the injection, and then showed a tendency to rapidly clear away in 60 minutes. These results suggest that Compounds 1, 2 and 3 possess excellent transferability to brain and rapid clearance from brain like [$^{123}$I]-IMPY.

TABLE 3

Radioactive accumulation in brain of the present compound after intravenous injection (rats)

| | | Radioactive accumulation per unit weight (% ID/g) | | | |
|---|---|---|---|---|---|
| | Compound | After 2 min. | After 5 min. | After 30 min. | After 60 min. |
| Example 19 | Compound 1 | 0.74 | 0.53 | 0.11 | 0.03 |
| Example 20 | Compound 2 | 0.42 | 0.26 | 0.04 | 0.02 |
| Example 21 | Compound 3 | 0.70 | 0.53 | 0.08 | 0.03 |
| Example 22 | Compound 4 | 0.80 | 0.61 | 0.12 | 0.03 |
| Comparative Example 2 | $^{123}$I-IMPY | 1.19 | 0.97 | 0.23 | 0.09 |

EXAMPLES 23 TO 25

Confirmation of Imaging of Amyloid in Brain with Compounds 1, 2 and 4

The following experiment was carried out in order to examine whether amyloid in brain can be imaged by the compound of the present invention.

Method (1) Aβ$_{1-42}$ (manufactured by Wako) was dissolved in phosphate buffer (pH 7.4) and shaken at 37° C. for 72 hours, to obtain a 1 mg/mL suspension of aggregated Aβ (hereinafter referred to as amyloid suspension in the Examples).

(2) Under thiopental anesthesia, 2.5 µL (corresponding to 25 µg) of the amyloid suspension was injected into an amygdaloid nucleus on one side of a male Wistar rat (7-week old). As a control, 2.5 µL of a phosphate buffered physiological saline solution (pH 7.4) was injected into an amygdaloid nucleus on the other side of the rat. The rats were examined 1 day after the injection of the amyloid suspension and the phosphate buffered physiological saline solution (pH 7.4).

(3) Compound 1 in a 10 mg/mL ascorbic acid-containing physiological saline solution (24 MBq/mL in radioactivity concentration), Compound 2 in a 10 mg/mL ascorbic acid-containing physiological saline solution (30 MBq/mL in radioactivity concentration) and Compound 4 in a 10 mg/mL ascorbic acid-containing physiological saline solution (32 MBq/mL in radioactivity concentration) were each prepared to obtain a sample solution. This sample solution was injected under thiopental anesthesia into the rat through the tail vein (dosage: 0.5 mL, dosed radioactivity: 12-15 MBq equivalent).

(4) Brain was removed 60 minutes after the injection to prepare a brain slice of 10 µm in thickness with a microtome (type: CM3050S, manufactured by LEICA). The brain slice was exposed to an imaging plate for 20 hours, and then image analysis was carried out by use of a Bio-imaging Analyzer (type: BAS-2500; manufactured by FUJIFILM Corporation).

(5) After the completion of the image analysis using the Bio-imaging Analyzer, pathological staining with Thioflavin T was carried out to perform imaging by use of a fluorescence microscope (manufactured by NIKON Corporation; type: TE2000-U model; excitation wavelength: 400-440 nm; detection wavelength: 470 nm). Thus, it was confirmed that amyloid was deposited on the slice (FIG. 10b, FIG. 11b and FIG. 12b).

Results

FIGS. 10-12 show images resulting from the autoradiogram and Thioflavin T staining. As shown in this figure, a marked accumulation of radioactivity was observed in the amygdaloid nucleus on the side to which the amyloid suspension was injected. From the result of Thioflavin T staining in the site where radioactivity was accumulated, it was confirmed that amyloid was present in the site. On the other hand, no significant accumulation of radioactivity was observed in the amygdaloid nucleus on the side to which the physiological saline solution was injected, compared with the other sites.

These results suggest that Compounds 1, 2 and 4 have a property of accumulating at intracerebral amyloid and has a capability of imaging intracerebral amyloid.

EXAMPLE 26

Confirmation of Imaging of Amyloid in Brain with Compound 3

The procedure was conducted in the same manner as in Example 23 except that a solution of Compound 3 in 10 mg/mL ascorbic acid-containing physiological saline solution (32 MBq/mL in radioactive concentration) was used as a sample solution, and a brain was removed 120 minutes after injection of the sample solution.

FIG. 13 shows images resulting from the autoradiogram and Thioflavin T staining. As shown in this figure, a marked accumulation of radioactivity was observed in the amygdaloid nucleus on the side to which the amyloid suspension was injected. From the result of Thioflavin T staining in the site where radioactivity was accumulated, it was confirmed that amyloid was present in the site. On the other hand, no significant accumulation of radioactivity was observed in the amygdaloid nucleus on the side to which the physiological saline solution was injected, compared with the other sites.

These results suggest that Compound 3 has a property of accumulating at intracerebral amyloid and has a capability of imaging intracerebral amyloid.

EXAMPLE 27

Reverse Mutation Test

In order to examine gene mutagenicity of Compound 5, reverse mutation test using *Salmonella typhimurium* TA98 and TA100, TA1535, TA1537 and *Escherichia coli* WP2uvrA (hereinafter referred to as Ames test) was conducted.

The test was conducted without addition of S9mix and with addition of S9mix. Dimethylsulfoxide (DMSO) was used as a negative control.

As a sample solution to be added to a test plate, a 50 mg/mL solution of Compound 5 in DMSO and solutions obtained by diluting this solution with DMSO to have various concentrations were prepared. For positive control without addition of S9mix, when TA98 was used as a test strain, a solution of AF-2 (compound concentration: 1 μg/mL) in DMSO was prepared and used as a sample solution; when TA100 or WP2uvrA was used as a test strain, a solution of AF-2 (compound concentration: 0.1 μg/mL) in DMSO was prepared and used as a sample solution; when TA1535 was used as a test strain, a solution of $NaN_3$ (compound concentration: 5 μg/mL) in water for injection was prepared and used as a sample solution; and when TA1537 was used as a test strain, a solution of 9AA (compound concentration: 800 μg/mL) in DMSO was prepared and used as a sample solution. For positive control with addition of S9mix, when TA98 was used as a test strain, a solution of 2-AA (compound concentration: 5 μg/mL) in DMSO was prepared and used as a sample solution; when TA100 was used as a test strain, a solution of 2-AA (compound concentration: 10 μg/mL) in DMSO was prepared and used as a sample solution; when WP2uvrA was used as a test strain, a solution of 2-AA (compound concentration: 100 μg/mL) in DMSO was prepared and used as a sample solution; and when TA1535 or TA1537 was used as a test strain, a solution of 2-AA (compound concentration: 20 μg/mL) in DMSO was prepared and used as a sample solution.

The addition amount of each sample to be examined was 0.1 mL/plate, and for negative control, only DMSO was added in an amount of 0.1 mL/plate. After each sample solution to be examined and a test strain were mixed together, the mixture was multilayered using soft agar on a medium of a test plate, and then incubated at 37° C. for 48 hours. Separately, after each sample solution to be examined, S9mix and a test strain were mixed together, the mixture was multilayered using soft agar on a medium of a test plate, and then incubated at 37° C. for 48 hours. Judgment was made by counting the number of reverse mutation colonies on the plate after the incubation, and when the number of reverse mutation colonies showed a value not less than two times the number in negative control and increased in a concentration-dependent manner, mutagenicity was determined to be positive.

The results are shown in Table 4. The number of reverse mutation colonies in the group treated with Compound 5 was less than two times the group treated with the negative control, regardless of addition of S9mix and the addition amount of a sample to be tested. On the other hand, the group treated with the positive control showed obvious increase in the number of reverse mutation colonies. From the aforementioned results, it is judged that Compound 5 is negative in the Ames test and has no mutagenicity.

TABLE 4

Results of Ames test

| | Mutagenicity | | | | | | | | | |
|---|---|---|---|---|---|---|---|---|---|---|
| | Without addition of S9mix | | | | With addition of S9mix | | | | | |
| | TA100 | TA1535 | WP2uvrA | TA98 | TA1537 | TA100 | TA1535 | WP2uvrA | TA98 | TA1537 |
| Example 27 | Negative | Negative | Negative | Negative | Negative | Negative | Negative | Negative | Negative | Negative |

EXAMPLE 28

Confirmation of binding to amyloid in brain with 2-[4'-(2''-hydroxyethoxy)-2'-methoxyphenyl]-6-[$^{123}$I]iodoimidazo[1,2-a]pyridine The following experiment was carried out in order to examine whether the compound of the present invention binds to amyloid in brain.

Method (1) $Aβ_{1-42}$ (manufactured by Wako) was dissolved in phosphate buffer (pH 7.4) and shaken at 37° C. for 72 hours, to obtain a 1 mg/mL suspension of aggregated Aβ (hereinafter referred to as amyloid suspension in the present Example).

(2) Under thiopental anesthesia, the 2.5 μL (corresponding to 25 μg) of the amyloid suspension was injected into an amygdaloid nucleus on one side of a male Wistar rat (7-week old). As a control, 2.5 μL of a phosphate buffered physiological saline solution (pH 7.4) was injected into an amygdaloid nucleus on the other side of the rat. A brain was removed from the rat a day after the injection of an amyloid suspension and a phosphate buffered physiological saline solution (pH 7.4) to prepare a brain slice of 10 μm in thickness with a microtome (type: CM3050S, manufactured by LEICA).

(3) Compound 6 in diethylether solution was diluted with a 1% bovine serum albumin/phosphate buffer (hereinafter referred to as 1% PB/BSA in the present Example) to obtain a sample solution (0.1 MBq/mL in radioactivity concentration).

(4) The above brain slice was immersed in phosphate buffer (pH7.4) for 30 minutes, and then immersed in a 1% bovine serum albumin/phosphate buffer (hereinafter referred to as 1% PB/BSA in the present Example) for 30 minutes. Then, the brain slice was immersed in a sample solution.

(5) The brain slice obtained above in (4) was immersed in a 1% PB/BSA for 5 minutes and in a phosphate buffer for 10 minutes (5 min.×2), and then air dried. Then, the brain slice was exposed to an imaging plate for 16 hours, and then image analysis was carried out by use of a Bio-imaging Analyzer (type: BAS-2500; manufactured by FUJIFILM Corporation).

(5) After the completion of the image analysis using the Bio-imaging Analyzer, pathological staining with Thioflavin T was carried out to perform imaging by use of a fluorescence microscope (manufactured by NIKON Corporation; type: TE2000-U model; excitation wavelength: 400-440 nm; detection wavelength: 470 nm). Thus, it was confirmed that amyloid was deposited on the slice (FIG. 14b).

Results

FIG. 14 shows images by the in vitro autoradiogram and Thioflavin T staining of the brain slice of the rat to which amyloid was injected intracerebrally. As shown in this figure, a marked accumulation of radioactivity was observed in the amygdaloid nucleus on the side to which the amyloid suspension was injected. From the result of Thioflavin T staining in the site where radioactivity was accumulated, it was confirmed that amyloid was present in the site. On the other hand, no significant accumulation of radioactivity was observed in the amygdaloid nucleus on the side to which the physiological saline solution was injected, compared with the other sites.

These results suggest that 2-[4'-(2"-hydroxyethoxy)-2'-methoxyphenyl]-6-[$^{123}$I]iodoimidazo[1,2-a]pyridine possesses a property of binding to intracerebral amyloid.

INDUSTRIAL APPLICABILITY

The compounds of the present invention can be utilized in the field of diagnostic agents.

Figure 1:
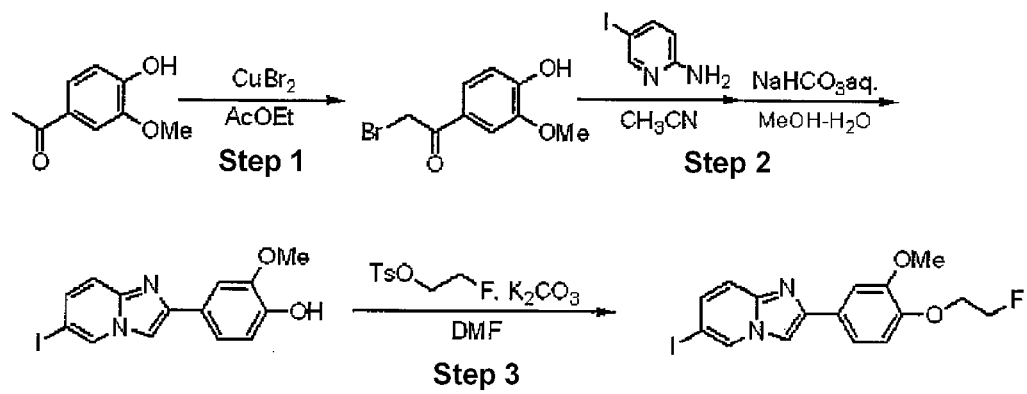
FIG. 1 is a scheme of synthesis of 2-[4'-(2"-fluoroethoxy)-3'-methoxyphenyl]-6-iodoimidazo[1,2-a]pyridine (non-radioactive iodinated form).
Figure 2:
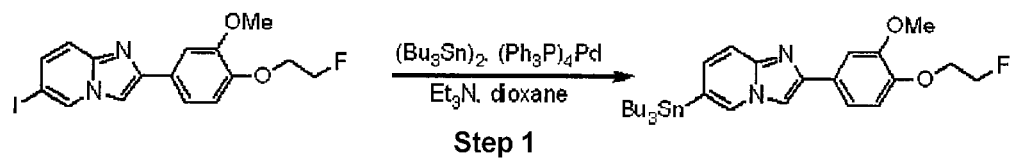
FIG. 2 is a scheme of synthesis of 6-tributylstannyl-2-[4'-(2"-fluoroethoxy)-3'-methoxyphenyl]imidazo[1,2-a]pyridine.
Figure 3:
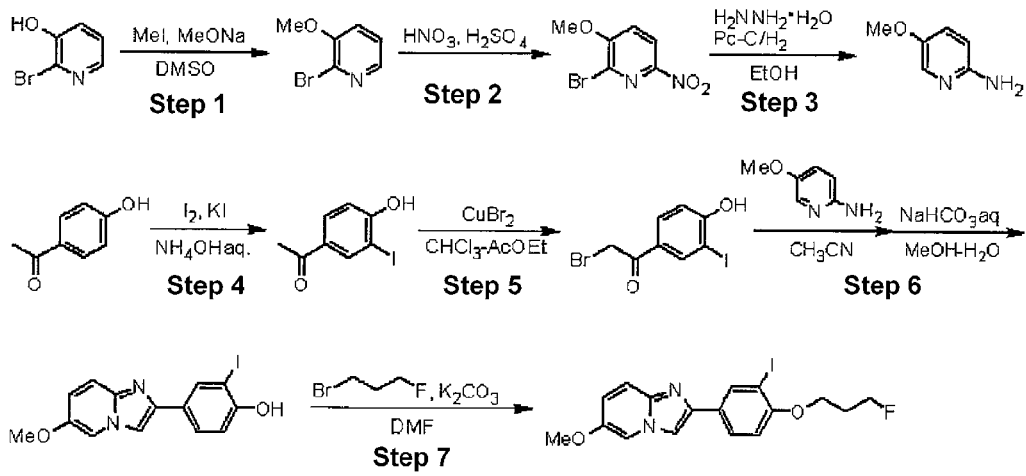
FIG. 3 is a scheme of synthesis of 2-[4'-(3"-fluoropropoxy)-3'-iodophenyl)-6-methoxyimidazo[1,2-a]pyridine (non-radioactive iodinated form).
Figure 4:
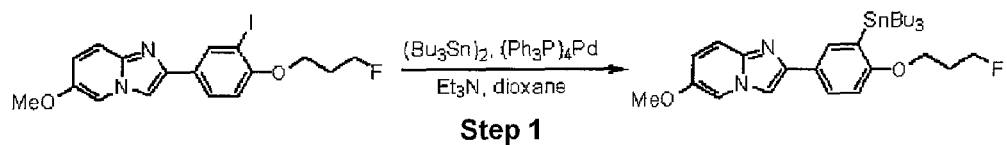
FIG. 4 is a scheme of synthesis of 2-[3'-tributylstannyl-4'-(3"-fluoropropoxy)phenyl]-6-methoxyimidazo[1,2-a]pyridine.
Figure 5:
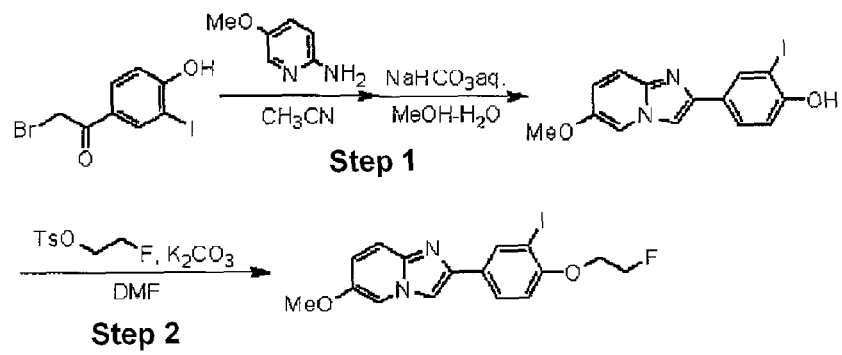
FIG. 5 is a scheme of synthesis of 2-[4'-(2"-fluoroethoxy)-3'-iodophenyl]-6-methoxyimidazo[1,2-a]pyridine (non-radioactive iodinated form).
Figure 6:
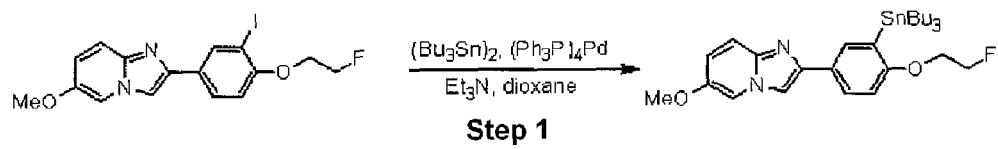
FIG. 6 is a scheme of synthesis of 2-[3'-tributylstannyl-4'-(2"-fluoroethoxy)phenyl]-6-methoxyimidazo[1,2-a]pyridine.
Figure 7:
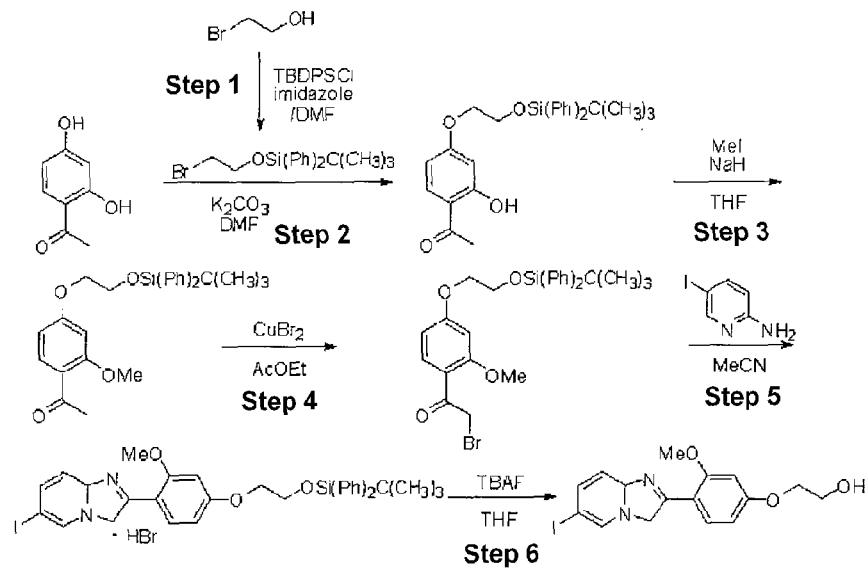
FIG. 7 is a scheme of synthesis of 2-[4'-(2"-hydroxyethoxy)-2'-methoxyphenyl]-6-iodoimidazo[1,2-a]pyridine (non-radioactive iodinated form).
Figure 8:
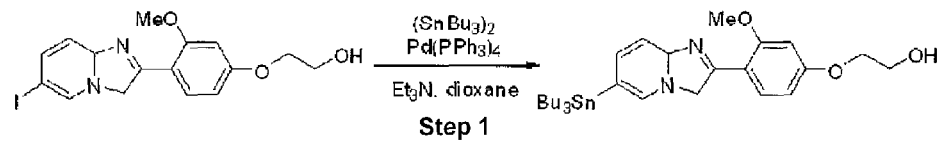
FIG. 8 is a scheme of synthesis of 6-tributylstannyl-2-[4'-(2"-hydroxyethoxy)-2'-methoxyphenyl]imidazo[1,2-a]pyridine.
Figure 9:
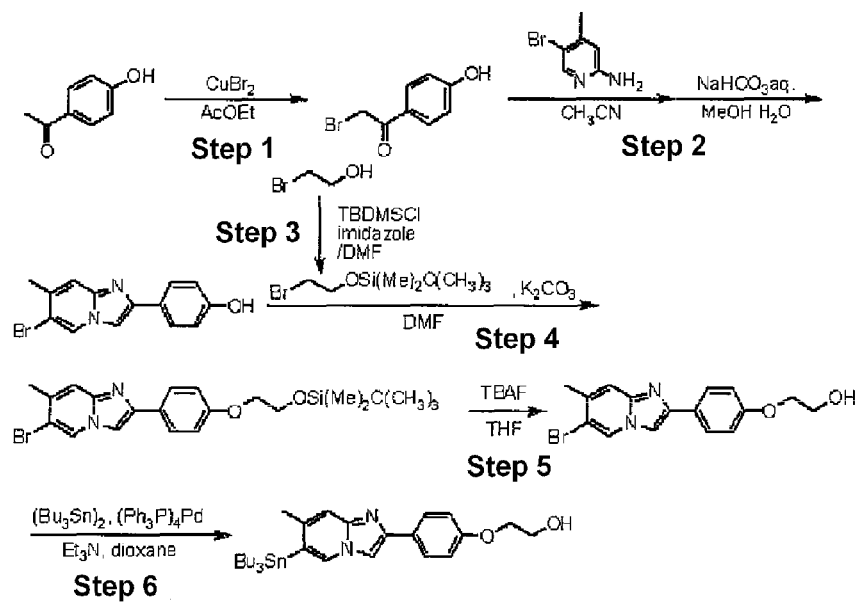
FIG. 9 is a scheme of synthesis of 6-tributylstannyl-2-[4'-(2"-hydroxyethoxy)phenyl]-7-methylimidazo[1,2-a]pyridine.
Figure 10:
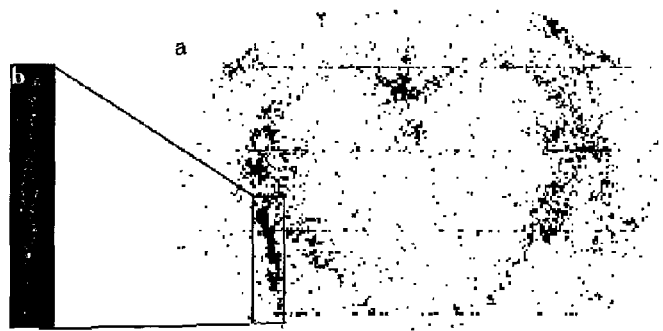
FIG. 10(a) is an autoradiogram of the brain slice after the injection of 2-[4'-(3"-fluoropropoxy)-3'-[$^{123}$I]iodophenyl]-6-methoxyimidazo[1,2-a]pyridine.
FIG. 10(b) is a fluorescent microscopic image of the Thioflavin T stained sample (a magnification of the site to which the amyloid suspension was injected).
Figure 11:
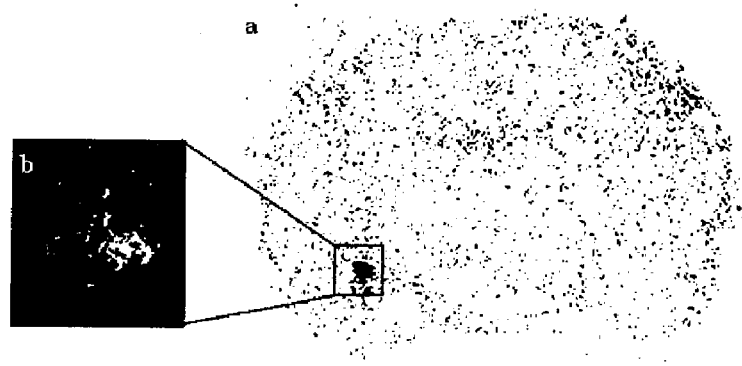
FIG. 11(a) is an autoradiogram of the brain slice after the injection of 2-[4'-(2"-fluoroethoxy)-3'-methoxyphenyl]-6-[$^{123}$I]iodoimidazo[1,2-a]pyridine.
FIG. 11(b) is a fluorescent microscopic image of the Thioflavin T stained sample (a magnification of the site to which the amyloid suspension was injected).
Figure 12:
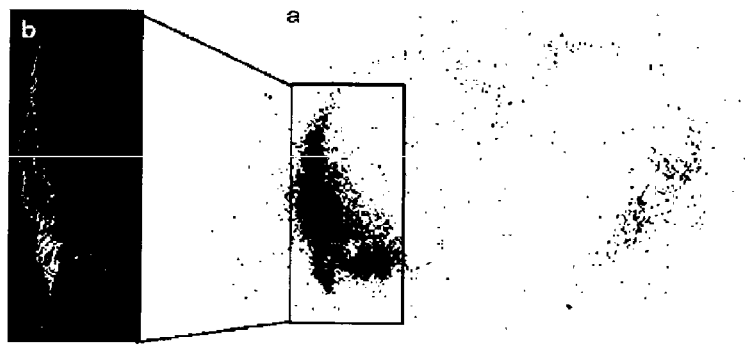
FIG. 12(a) is an autoradiogram of the brain slice after the injection of 2-[4'-(2"-hydroxyethoxy)phenyl]-6-[$^{123}$I]iodo-7-methylimidazo[1,2-a]pyridine.
FIG. 12(b) is a fluorescent microscopic image of the Thioflavin T stained sample (a magnification of the site to which the amyloid suspension was injected).
Figure 13:
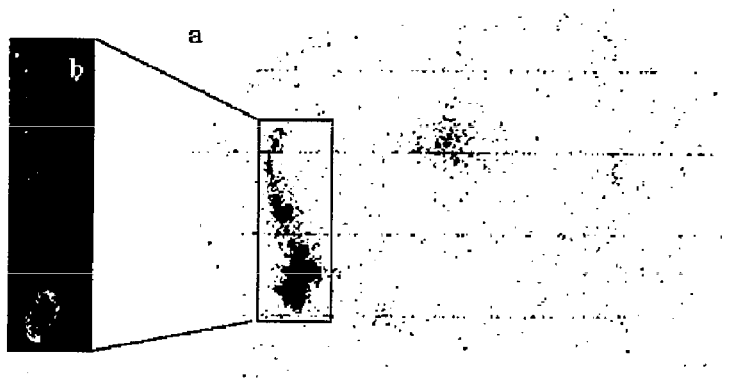
FIG. 13(a) is an autoradiogram of the brain slice after the injection of 2-[4'-(2"-fluoroethoxy)-3'-[$^{123}$I]iodophenyl]-6-methoxyimidazo[1,2-a]pyridine.
FIG. 13(b) is a fluorescent microscopic image of the Thioflavin T stained sample (a FIG. 14(a) is an in vitro autoradiogram of the brain slice of 2-[4'-(2"-hydroxyethoxy)-2'-methoxyphenyl]-6-[$^{123}$I]iodoimidazo[1,2-a]pyridine, and FIG. 14(b) is a fluorescent microscopic image of the Thioflavin T stained sample (a magnification of the site to which the amyloid suspension was injected).
Figure 14:
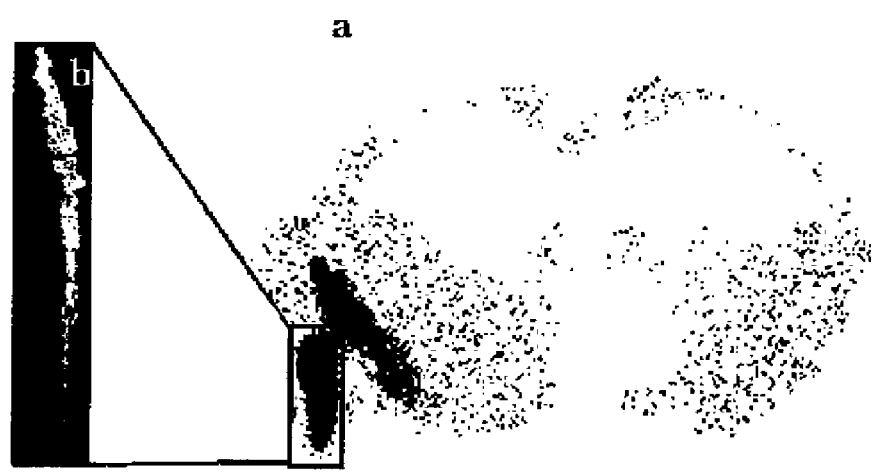

The invention claimed is:

1. A compound represented by the following formula (1), and a salt thereof:

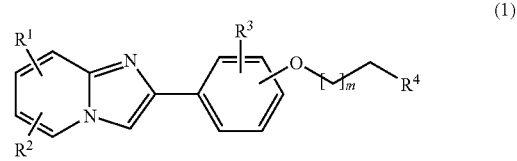

(1)

wherein $R^1$, $R^2$ and $R^3$ each independently represents a group selected from the group consisting of a hydrogen, a hydroxyl group, an alkyl substituent with 1 to 4 carbon atoms, an alkoxy substituent having an alkyl chain with 1 to 4 carbon atoms and a halogen substituent, excluding the case where two or more of the substituents $R^1$, $R^2$ and $R^3$ are hydrogen, $R^4$ is a group selected from the group consisting of a hydrogen, a hydroxyl group, an alkoxy group having an alkyl chain with 1 to 4 carbon atoms and a halogen substituent, and m is an integer of 1 to 4, provided that at least one of $R^1$, $R^2$, $R^3$ and $R^4$ represents a radioactive halogen substituent.

2. The compound and a salt thereof according to claim 1, wherein at least one of $R^1$, $R^2$, $R^3$ and $R^4$ represents a radioactive halogen selected from the group consisting of $^{18}$F, $^{76}$Br, $^{123}$I, $^{124}$I, $^{125}$I or $^{131}$I.

3. The compound and a salt thereof according to claim 2, which is selected from the group consisting of 2-[4'-(3"-fluoropropoxy)-3'-[$^{123}$I]iodophenyl]-6-methoxyimidazo[1,2-a]pyridine, 2-[4'-(2"-fluoroethoxy)-3'-methoxyphenyl]-6-[$^{123}$I]iodoimidazo[1,2-a]pyridine, 2-[4'-(2"-fluoroethoxy)-3'-[$^{123}$I]iodophenyl]-6-methoxyimidazo[1,2-a]pyridine, 2-[4'-(2"-hydroxyethoxy)phenyl]-6-[$^{123}$I]iodo-7-methylimidazo[1,2-a]pyridine, and 2-[4'-(2"-hydroxyethoxy)-2'-methoxyphenyl]-6-[$^{123}$I]iodoimidazo[1,2-a]pyridine.

4. A compound represented by the following formula (2), and a salt thereof:

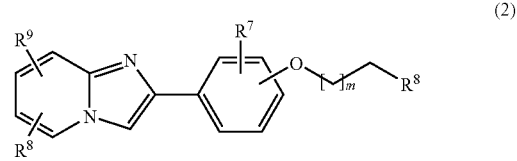

(2)

wherein $R^6$ and $R^7$ each independently represents a group selected from the group consisting of a hydrogen, a hydroxyl group, an alkyl substituent with 1 to 4 carbon atoms, an alkoxy substituent having an alkyl chain with 1 to 4 carbon atoms and a halogen substituent, excluding the case where both $R^6$ and $R^7$ are hydrogen, $R^8$ is a group selected from the group consisting of a hydrogen, a hydroxyl group, an alkoxy substituent having an alkyl chain with 1 to 4 carbon atoms and a halogen substituent, $R^9$ is a group selected from the group consisting of a non-radioactive halogen substituent, a nitro group, a trialkylammonium group having alkyl chains with 1 to 4 carbon atoms, a trialkylstannyl substituent having alkyl chains with 1 to 4 carbon atoms or a triphenylstannyl group, and m is an integer of 1 to 4.

5. A compound represented by the following formula (3), and a salt thereof:

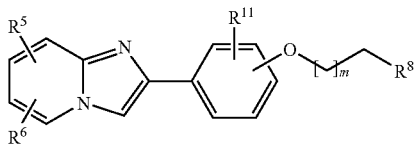

(3)

wherein $R^5$ and $R^6$ each independently represents a group selected from the group consisting of a hydrogen, a hydroxyl group, an alkyl substituent with 1 to 4 carbon atoms, an alkoxy substituent having an alkyl chain with 1 to 4 carbon atoms and a halogen substituent, excluding the case where both $R^5$ and $R^6$ are hydrogen, $R^8$ is a group selected from the group consisting of a hydrogen, a hydroxyl group, an alkoxy substituent having an alkyl chain with 1 to 4 carbon atoms and a halogen substituent, $R^{11}$ is a group selected from the group consisting of a non-radioactive halogen substituent, a nitro group, a trialkylammonium group having alkyl chains with 1 to 4 carbon atoms, a trialkylstannyl substituent having alkyl chains with 1 to 4 carbon atoms or a triphenylstannyl group, and m is an integer of 1 to 4.

6. A compound represented by the following formula (4), and a salt thereof:

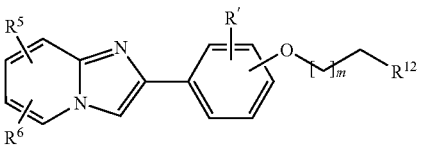

(4)

wherein $R^5$, $R^6$ and $R^7$ each independently represents a group selected from the group consisting of a hydrogen, a hydroxyl group, an alkyl substituent with 1 to 4 carbon atoms, an alkoxy substituent having an alkyl chain with 1 to 4 carbon atoms and a halogen substituent, excluding the case where two or more of the substituents $R^5$, $R^6$ and $R^7$ are hydrogen, $R^{12}$ is a group selected from the group consisting of a methanesulfonyloxy substituent, a trifluoromethanesulfonyloxy substituent and an aromatic sulfonyloxy substituent, and m is an integer of 1 to 4.

7. A reagent for detecting amyloid deposited on a biological tissue, comprising a compound represented by the following formula (1):

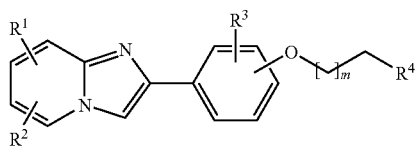

(1)

wherein $R^1$, $R^2$ and $R^3$ each independently represents a group selected from the group consisting of a hydrogen, a hydroxyl group, an alkyl substituent with 1 to 4 carbon atoms, an alkoxy substituent having an alkyl chain with 1 to 4 carbon atoms and a halogen substituent, excluding the case where two or more of the substituents $R^1$, $R^2$ and $R^3$ are hydrogen, $R^4$ is a group selected from the group consisting of a hydrogen, a hydroxyl group, an alkoxy substituent having an alkyl chain with 1 to 4 carbon atoms and a halogen substituent, and m is an integer of 1 to 4, provided that at least one of $R^1$, $R^2$, $R^3$ and $R^4$ represents a radioactive halogen substituent.

8. The reagent for detecting amyloid deposited on a biological tissue, according to claim 7, wherein at least one of $R^1$, $R^2$, $R^3$ and $R^4$ represent a radioactive halogen selected from the group consisting of $^{18}F$, $^{76}Br$, $^{123}I$, $^{124}I$, $^{125}I$ or $^{131}I$.

9. The reagent for detecting amyloid deposited on a biological tissue, according to claim 7, which comprises a compound selected from the group consisting of 2-[4'-(3"-fluoropropoxy)-3'-[$^{123}$I]iodophenyl]-6-methoxyimidazo[1,2-a]pyridine, 2-[4'-(2"-fluoroethoxy)-3'-methoxyphenyl]-6-[$^{123}$I]iodoimidazo[1,2-a]pyridine, 2-[4'-(2"-fluoroethoxy)-3'-[$^{123}$I]iodophenyl]-6-methoxyimidazo[1,2-a]pyridine, 2-[4'-(2"-hydroxyethoxy)phenyl]-6-[$^{123}$I]iodo-7-methylimidazo[1,2-a]pyridine, and 2-[4'-(2"-hydroxyethoxy)-2'-methoxyphenyl]-6-[$^{123}$I]iodoimidazo[1,2-a]pyridine.

* * * * *